US008449991B2

(12) United States Patent
Gardinier et al.

(10) Patent No.: US 8,449,991 B2
(45) Date of Patent: May 28, 2013

(54) USE OF SN AND PORE SIZE CONTROL TO IMPROVE BIOCOMPATIBILITY IN POLYCRYSTALLINE DIAMOND COMPACTS

(75) Inventors: Clayton F. Gardinier, Lafayette, LA (US); Alfred S. Despres, Heber, UT (US); Troy J. Medford, Orem, UT (US); Tim Bunton, Norfolk, VA (US)

(73) Assignee: Dimicron, Inc., Orem, UT (US)

( * ) Notice: Subject to any disclaimer, the term of this patent is extended or adjusted under 35 U.S.C. 154(b) by 1054 days.

(21) Appl. No.: 12/422,203

(22) Filed: Apr. 10, 2009

(65) Prior Publication Data

US 2009/0263643 A1    Oct. 22, 2009

Related U.S. Application Data

(63) Continuation-in-part of application No. 11/398,462, filed on Apr. 5, 2006, now Pat. No. 7,678,325.

(60) Provisional application No. 60/669,082, filed on Apr. 7, 2005.

(51) Int. Cl.
*B32B 9/00* (2006.01)
*B32B 19/00* (2006.01)
*B32B 5/18* (2006.01)
*B22F 3/10* (2006.01)
*B22F 3/00* (2006.01)
*B22F 5/00* (2006.01)

(52) U.S. Cl.
USPC ........... 428/697; 428/550; 428/551; 428/613; 428/634; 428/646; 623/18.11; 623/23.51; 623/23.53; 623/23.56

(58) Field of Classification Search
None
See application file for complete search history.

(56) References Cited

U.S. PATENT DOCUMENTS

| 2,254,549 A | 9/1941 | Small |
| 2,947,608 A | 8/1960 | Hall |
| 2,947,609 A | 8/1960 | Strong |

(Continued)

FOREIGN PATENT DOCUMENTS

| GB | 2 283 772 | 5/1995 |
| GB | 2 290 326 | 12/1995 |

(Continued)

OTHER PUBLICATIONS

U.S. Appl. No. 11/435,383, filed May 16, 2006, Pope et al.

(Continued)

*Primary Examiner* — Jonathan Langman
(74) *Attorney, Agent, or Firm* — Pate Peterson, PLLC; Brett Peterson

(57) ABSTRACT

Polycrystalline diamond compacts for use in artificial joints achieve reduced corrosion and improved biocompatibility through the use of solvent metal formulations containing tin and through the control of solvent metal pore size, particularly in inner layers of the compact. Solvent metal formulations containing tin have been discovered which provide sintering ability, part strength, and grind resistance comparable to levels achieved by using CoCrMo solvent metals. It has been discovered that limiting the solvent metal pore size in the diamond layers minimizes or eliminates the occurrence of micro cracks in the solvent metal and significantly reduces the corrosion of the compact as manifested by the release of heavy metal ions from the compact. Polycrystalline diamond compacts which utilize both the solvent metal formulations containing tin and the control of pore sizes achieve significantly reduced corrosion and improved biocompatibility compared to prior art polycrystalline diamond compacts.

23 Claims, 16 Drawing Sheets

U.S. PATENT DOCUMENTS

| | | |
|---|---|---|
| 2,947,610 A | 8/1960 | Hall et al. |
| 2,947,611 A | 8/1960 | Bundy |
| 2,992,900 A | 7/1961 | Bovenkerk |
| 3,031,269 A | 4/1962 | Bovenkerk |
| 3,115,729 A | 12/1963 | Render |
| 3,297,407 A | 1/1967 | Wentorf, Jr. |
| 3,423,177 A | 1/1969 | Bovenkerk |
| 3,488,153 A | 1/1970 | Bundy |
| 3,574,580 A | 4/1971 | Stromberg et al. |
| 3,597,158 A | 8/1971 | Horton |
| 3,656,184 A | 4/1972 | Chambers |
| 3,702,573 A | 11/1972 | Nemeth |
| 3,819,814 A | 6/1974 | Pope |
| 3,864,409 A | 2/1975 | Pope |
| 3,865,585 A | 2/1975 | Rademacher |
| 3,916,497 A | 11/1975 | Doi |
| 4,012,229 A | 3/1977 | Herchenroeder et al. |
| 4,089,933 A | 5/1978 | Vereschagin et al. |
| 4,104,344 A | 8/1978 | Pope et al. |
| 4,104,441 A | 8/1978 | Fedoseev et al. |
| 4,163,769 A | 8/1979 | Pope et al. |
| 4,231,762 A | 11/1980 | Hara et al. |
| 4,259,072 A | 3/1981 | Hirabayashi et al. |
| 4,260,203 A | 4/1981 | Garner |
| 4,260,397 A | 4/1981 | Bovenkerk |
| 4,380,471 A | 4/1983 | Lee et al. |
| 4,406,871 A | 9/1983 | Samoilovich et al. |
| 4,410,054 A | 10/1983 | Nagel et al. |
| 4,454,612 A | 6/1984 | McDaniel et al. |
| 4,470,158 A | 9/1984 | Pappas et al. |
| 4,518,659 A | 5/1985 | Gigl et al. |
| 4,525,178 A | 6/1985 | Hall |
| 4,525,179 A | 6/1985 | Gigl |
| 4,604,106 A | 8/1986 | Hall et al. |
| 4,610,699 A | 9/1986 | Yazu et al. |
| 4,662,348 A | 5/1987 | Hall et al. |
| 4,668,290 A | 5/1987 | Wang et al. |
| 4,714,468 A | 12/1987 | Wang et al. |
| 4,714,473 A | 12/1987 | Bloebaum |
| 4,729,440 A | 3/1988 | Hall |
| 4,755,185 A | 7/1988 | Tarr |
| 4,778,486 A | 10/1988 | Csillag et al. |
| 4,802,539 A | 2/1989 | Hall et al. |
| 4,808,185 A | 2/1989 | Penenberg et al. |
| 4,822,365 A | 4/1989 | Walker et al. |
| 4,822,366 A | 4/1989 | Bolesky |
| 4,865,603 A | 9/1989 | Noiles |
| 4,925,701 A | 5/1990 | Jansen et al. |
| 4,931,068 A | 6/1990 | Dismukes et al. |
| 4,979,957 A | 12/1990 | Hodorek |
| 5,002,577 A | 3/1991 | Bolesky et al. |
| 5,002,731 A | 3/1991 | Crook et al. |
| 5,009,673 A | 4/1991 | Cho |
| 5,011,515 A | 4/1991 | Frushour |
| 5,030,233 A | 7/1991 | Ducheyne |
| 5,037,423 A | 8/1991 | Kenna |
| 5,082,359 A | 1/1992 | Kirkpatrick |
| 5,092,687 A | 3/1992 | Hall |
| 5,108,432 A | 4/1992 | Gustavson |
| 5,128,146 A | 7/1992 | Hirayama et al. |
| 5,133,757 A | 7/1992 | Sioshansi et al. |
| 5,152,794 A | 10/1992 | Davidson |
| 5,152,795 A | 10/1992 | Sioshansi et al. |
| 5,154,023 A | 10/1992 | Sioshansi |
| 5,180,394 A | 1/1993 | Davidson |
| 5,181,926 A | 1/1993 | Koch et al. |
| 5,192,323 A | 3/1993 | Shetty et al. |
| 5,211,726 A | 5/1993 | Slutz et al. |
| 5,236,545 A | 8/1993 | Pryor |
| 5,248,317 A | 9/1993 | Tank et al. |
| 5,254,509 A | 10/1993 | Gesing et al. |
| 5,258,022 A | 11/1993 | Davidson |
| 5,278,109 A | 1/1994 | Ono et al. |
| 5,308,412 A | 5/1994 | Shetty et al. |
| 5,310,408 A | 5/1994 | Schryver et al. |
| 5,330,481 A | 7/1994 | Hood et al. |
| 5,330,826 A | 7/1994 | Taylor et al. |
| 5,355,969 A | 10/1994 | Hardy et al. |
| 5,358,525 A | 10/1994 | Fox et al. |
| 5,370,694 A | 12/1994 | Davidson |
| 5,372,660 A | 12/1994 | Davidson et al. |
| 5,380,547 A | 1/1995 | Higgins |
| 5,383,934 A | 1/1995 | Armini et al. |
| 5,387,247 A | 2/1995 | Vallana et al. |
| 5,391,407 A | 2/1995 | Dearnaley |
| 5,391,408 A | 2/1995 | Piera |
| 5,391,409 A | 2/1995 | Shibata et al. |
| 5,391,422 A | 2/1995 | Omori et al. |
| 5,414,049 A | 5/1995 | Sun et al. |
| 5,415,704 A | 5/1995 | Davidson |
| 5,458,827 A | 10/1995 | Holly |
| 5,478,906 A | 12/1995 | Howard, Jr. |
| 5,480,683 A | 1/1996 | Chabrol et al. |
| 5,507,804 A | 4/1996 | Llanos |
| 5,507,814 A | 4/1996 | Gilbert et al. |
| 5,507,824 A | 4/1996 | Lennox |
| 5,508,368 A | 4/1996 | Knapp et al. |
| 5,512,235 A | 4/1996 | Cerutti et al. |
| 5,530,072 A | 6/1996 | Shirodkar |
| 5,554,415 A | 9/1996 | Turchan et al. |
| 5,571,616 A | 11/1996 | Phillips et al. |
| 5,593,719 A | 1/1997 | Dearnaley et al. |
| 5,620,754 A | 4/1997 | Turchan et al. |
| 5,628,824 A | 5/1997 | Vohra et al. |
| 5,635,243 A | 6/1997 | Turchan et al. |
| 5,641,323 A | 6/1997 | Caldarise |
| 5,643,641 A | 7/1997 | Turchan et al. |
| 5,645,601 A | 7/1997 | Pope et al. |
| 5,682,595 A | 10/1997 | Gonseth et al. |
| 5,702,448 A | 12/1997 | Buechel et al. |
| 5,725,573 A | 3/1998 | Dearnaley et al. |
| 5,766,394 A | 6/1998 | Anderson et al. |
| 5,773,140 A | 6/1998 | Cerutti et al. |
| 5,780,119 A | 7/1998 | Dearnaley et al. |
| 5,824,651 A | 10/1998 | Nanci et al. |
| 5,830,539 A | 11/1998 | Yan et al. |
| 5,855,996 A | 1/1999 | Corrigan et al. |
| 5,868,796 A | 2/1999 | Buechel et al. |
| 5,871,547 A | 2/1999 | Abouaf et al. |
| 5,895,388 A | 4/1999 | Zobel |
| 5,895,428 A | 4/1999 | Berry |
| 5,916,269 A | 6/1999 | Serbousek et al. |
| 5,947,893 A | 9/1999 | Agrawal et al. |
| 5,981,827 A | 11/1999 | Devilin et al. |
| 6,010,533 A | 1/2000 | Pope et al. |
| 6,063,149 A | 5/2000 | Zimmer |
| 6,077,148 A | 6/2000 | Klein et al. |
| 6,183,818 B1 | 2/2001 | Vohra et al. |
| 6,207,218 B1 | 3/2001 | Layrolle et al. |
| 6,221,108 B1 | 4/2001 | Smith |
| 6,290,726 B1 | 9/2001 | Pope et al. |
| 6,398,815 B1 | 6/2002 | Pope et al. |
| 6,402,787 B1 | 6/2002 | Pope et al. |
| 6,410,877 B1 | 6/2002 | Dixon et al. |
| 6,425,922 B1 | 7/2002 | Pope et al. |
| 6,488,715 B1 | 12/2002 | Pope et al. |
| 6,494,918 B1 | 12/2002 | Pope et al. |
| 6,497,727 B1 | 12/2002 | Pope et al. |
| 6,514,289 B1 | 2/2003 | Pope et al. |
| 6,517,583 B1 | 2/2003 | Pope et al. |
| 6,562,462 B2 | 5/2003 | Griffin et al. |
| 6,596,225 B1 | 7/2003 | Pope et al. |
| 6,610,095 B1 | 8/2003 | Pope et al. |
| 6,655,845 B1 | 12/2003 | Pope et al. |
| 6,676,704 B1 | 1/2004 | Pope et al. |
| 6,709,463 B1 | 3/2004 | Pope et al. |
| 6,773,520 B1 | 8/2004 | Fehring et al. |
| 6,793,681 B1 | 9/2004 | Pope et al. |
| 6,797,326 B2 | 9/2004 | Griffin et al. |
| 6,800,095 B1 | 10/2004 | Pope et al. |
| 6,817,550 B2 | 11/2004 | Taylor et al. |
| 7,077,867 B1 | 7/2006 | Pope et al. |
| 7,172,142 B2 | 2/2007 | Taylor et al. |
| 7,494,507 B2 | 2/2009 | Dixon et al. |
| 7,569,176 B2 | 8/2009 | Pope et al. |
| 7,608,333 B2 | 10/2009 | Eyre |
| 7,678,325 B2 | 3/2010 | Gardinier |

| | | |
|---|---|---|
| 7,726,421 B2 | 6/2010 | Middlemiss |
| 2002/0102403 A1 | 8/2002 | Leverenz et al. |
| 2003/0019106 A1 | 1/2003 | Pope et al. |
| 2003/0191533 A1* | 10/2003 | Dixon et al. .............. 623/17.14 |
| 2004/0111159 A1 | 6/2004 | Pope et al. |
| 2004/0199260 A1 | 10/2004 | Pope et al. |
| 2004/0223676 A1 | 11/2004 | Pope et al. |
| 2005/0087915 A1 | 4/2005 | Pope et al. |
| 2005/0110187 A1 | 5/2005 | Pope et al. |
| 2005/0121417 A1 | 6/2005 | Dixon et al. |
| 2005/0133277 A1 | 6/2005 | Dixon et al. |
| 2005/0146086 A1 | 7/2005 | Pope et al. |
| 2005/0158200 A1 | 7/2005 | Pope et al. |
| 2005/0203630 A1 | 9/2005 | Pope et al. |
| 2006/0263233 A1 | 11/2006 | Gardinier et al. |
| 2008/0302579 A1 | 12/2008 | Keshavan |

FOREIGN PATENT DOCUMENTS

| | | |
|---|---|---|
| GB | 2 290 327 | 12/1995 |
| GB | 2 290 328 | 12/1995 |
| JP | 01-116048 | 5/1989 |
| JP | 9173437 | 7/1997 |
| WO | WO 2009-027949 | 3/2009 |

OTHER PUBLICATIONS

U.S. Appl. No. 11/435,392, filed May 16, 2006, Pope et al.
U.S. Appl. No. 11/957,277, filed Dec. 14, 2007, Dixon et al.
RD 363004, Jul. 1994, Anonymous.
ISTA Symposium Presentation, Sep. 1997.
ISTA Symposium Presentation, Oct. 1998.

* cited by examiner

USE OF SN AND PORE SIZE CONTROL TO IMPROVE BIOCOMPATIBILITY IN POLYCRYSTALLINE DIAMOND COMPACTS

PRIORITY

The present application is a continuation-in-part of U.S. patent application Ser. No. 11/398,462, filed Apr. 5, 2006, now U.S. Pat. No. 7,678,325 which is expressly incorporated herein by reference, which claims the benefit of U.S. Provisional Patent Application Ser. No. 60/669,082, filed Apr. 7, 2005.

THE FIELD OF THE INVENTION

The present invention relates to the use of sintered polycrystalline diamond compacts for use in prosthetic joints. More specifically, the present invention relates to polycrystalline diamond compacts having improved biocompatibility.

BACKGROUND

Polycrystalline diamond is used in many demanding and abrasive applications such as oil well drilling and hard materials machining. Its superior mechanical properties and resistance to abrasion are suitable for bearing components in medical implant devices, such as artificial joints. One of the main obstacles in using PCD (polycrystalline diamond) in medical implant devices is that normal materials and processes to create PCD produce a material that is not biocompatible.

PCD is fabricated by subjecting unbonded diamond powder to extreme pressure and heat in the presence of a solvent metal. The powder is often placed adjacent to a substrate and surrounded by a refractory metal containment can. In some cases, a refractory metal layer is placed between the substrate and the inner diamond layer. The assembly (containment can, unbonded diamond powder and solvent metal, and the substrate) is placed in a high pressure cell and pressurized in a hydraulic press to more than 55 Kbar. The mixture is then heated to a temperature above the melting point of the solvent metal, at which point the solvent metal melts and flows or sweeps into the interstitial voids between adjacent diamond crystals. The solvent metal is driven by the pressure gradient to fill the voids.

Carbon atoms from the surface of the diamond crystals dissolve into the molten solvent metal, forming a carbon solution. When the proper temperature and pressure are reached, diamond formation is thermodynamically favored and the carbon that is held in solution in the molten solvent metal crystallizes out onto the diamond grains, bonding adjacent diamond grains together with diamond to diamond bonds. This forms a sintered polycrystalline diamond structure with the solvent metal in the interstitial spaces between the diamond grains. In addition to the crystallization of the dissolved diamond to bond adjacent diamond crystals, the dissolved carbon may react with the solvent metal to form metal carbides.

The diamond in the resulting sintered compact is highly inert and biocompatible. Thus, the exposed non-diamond constituents of the polycrystalline diamond compact such as the interstitial solvent metal in the PCD are what makes the PCD biocompatible or not.

One of the tests that is used to determine the biocompatibility of PCD, or other materials, is an elution test. In this test a PCD part or a portion thereof is placed in a container with a solution that is used to simulate body fluid. For this purpose, Hank's Balanced Salt Solution (HBSS) is often used as the solution for the elution test. Hank's solution contains a mix of salts and phosphates. A phosphate buffer can be added to stabilize the pH of the solution at a desired value. A controlled amount of solution is placed with the PCD part for a prescribed period of time, usually 24 hours. The amount and type of material that is released by the PCD and into the fluid through corrosion processes are measured, typically by Inductively Coupled Plasma Mass Spectroscopy (ICPMS).

Normal body pH is 7.4, but this pH fluctuates over time and can be significantly lower in local areas. In hematomas, where circulation in impaired, the pH may dip as low as 6 for a short period of time. For implants in the immediate post surgical time period, a hematoma like condition can exist around the implantation site. Thus, pH 6 is a worst case environmental condition that serves as an appropriate test case for corrosion resistance and elution testing. There is another advantage to using pH 6 as the elution test environment. For materials that are sensitive to pH, either due to natural material chemistry, electrocorrosion, crevice corrosion, or pitting mechanisms, testing under a slightly more acidic pH will show problems quickly that would take much longer tests in pH 7.4 to adequately demonstrate. Since implants are generally in place for many years, and hopefully the remainder of the patient's life, long term corrosion resistance is an essential part of implant material biocompatibility. It is for these reasons that elution tests are preferentially conducted at pH 6.

Release of metallic ions from medical devices is a long term concern that is well documented in the medical literature. Elevated serum metal ion concentrations are present in patients that have metal on metal hip and spine arthroplasty devices. The long term effect of these elevated levels is unknown, but potential increased risk for cancer and other malignancies remote from the implantation site are a real concern. Local acute toxicity effects of these devices can be observed in tissue directly surrounding these devices. Studies in the literature for patients with metal on metal hip implants report an increase in serum and urine Co and Cr levels of between 3 and 23 times relative to normal levels.

Some references indicating these elevated levels of Co and Cr are: Skipor, Anastasia, Pat Campbell, et al. *Metal Ion Levels in Patients with Metal on Metal Hip Replacements*. Society for Biomaterials 28th Meeting Transactions, 2002, and Josh Jacobs et al. Cobalt and *Chromium Concentrations in Patients with Metal on Metal Total Hip Replacements*. Clinical Orthopedics, S256-S263, 1996.

The traditional metals used in sintering diamond to make PCD are the first row transition metals in the periodic table. These most notably being cobalt, but also manganese, iron, and nickel for example. None of these metals are both corrosion resistant and biocompatible by themselves. Typically, metals may be made more corrosion resistant by adding elements that form stable oxide films to the metal. Chrome is the most notable element for this purpose. Chrome is added to steels to create stainless steels and it is added to cobalt to form biocompatible alloys used extensively in orthopedic implants such as CoCrMo ASTM F-75 or ASTM F-799.

It has been discovered that attempts to use alloys that contain chrome as a sintering metal to form PCD did not work as effectively as intended, and often resulted in PCD which was not fully biocompatible, as it suffered from corrosion and ion elution. One reason that these diamond compacts were not fully corrosion resistant is that chrome is a strong carbide former. During the sintering process, the chrome is exposed to the dissolved carbon which is held in solution in the molten solvent metal. When this occurs, chrome will precipitate out of the molten metal as chrome carbide. This leaves the original solvent metal, cobalt for example, depleted or devoid of chrome in some areas. This creates a PCD which has areas of exposed metal at the surface which are depleted in chrome and therefore with reduced corrosion protection or biocompatibility. It is thus appreciated that the attempts to find a solvent metal for sintering diamond into a biocompatible compact have been hindered by the reactions occurring between the metal and the diamond during sintering. The interstitial metal and carbides in the resulting sintered diamond compact are quite different than the solvent metals used as a starting material. As a result, metals which have good biocompatibility by themselves have proven to have poor biocompatibility after being used as a solvent metal in forming a sintered diamond compact.

SUMMARY OF THE INVENTION

It is an object of the present invention to provide a polycrystalline diamond compact which exhibits improved biocompatibility so as to be better suited for use in artificial joints. It is an object of the present invention to provide methods and materials for making corrosion resistant and biocompatible polycrystalline diamond using high pressure and high temperature processes, and to provide artificial joint components made by these methods and materials.

According to one aspect of the invention, a solvent metal composition is provided which has improved corrosion resistance and biocompatibility after sintering into a polycrystalline diamond compact.

According to another aspect of the invention, a polycrystalline diamond compact is provided with improved corrosion resistance and biocompatibility through reduction in micro cracks in the solvent metal.

These and other aspects of the present invention are realized in a polycrystalline diamond compact for prosthetic joint components as shown and described in the following figures and related description.

BRIEF DESCRIPTION OF THE DRAWINGS

Various embodiments of the present invention are shown and described in reference to the numbered drawings wherein.

Figure 1:
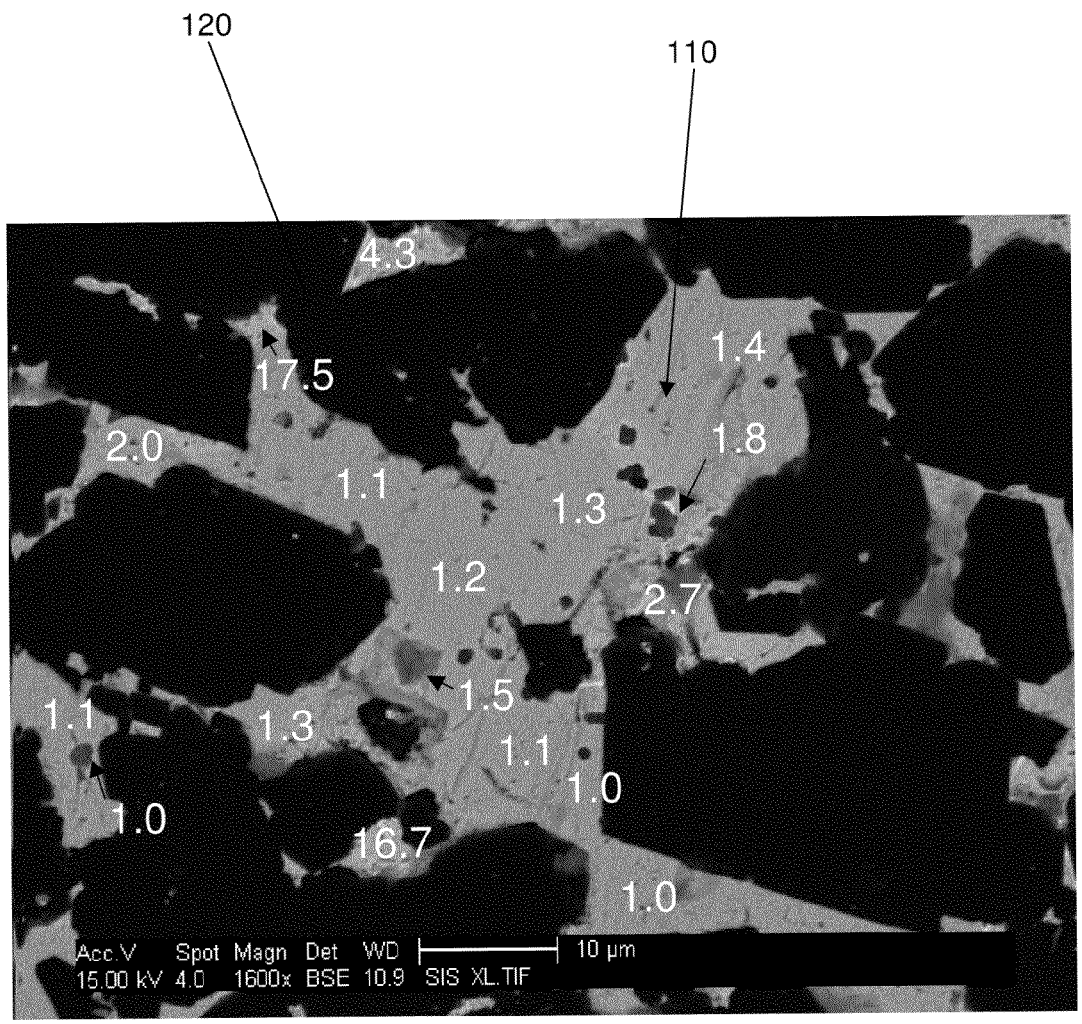
FIG. 1 shows a micrograph of a diamond layer of a PCD part.

It will be appreciated that the drawings are illustrative and not limiting of the scope of the invention which is defined by the appended claims. The embodiments shown accomplish various aspects and objects of the invention. It is appreciated that it is not possible to clearly show each element and aspect of the invention in a single figure, and as such, multiple figures are presented to separately illustrate the various details of the invention in greater clarity. Similarly, not every embodiment need accomplish all advantages of the present invention.

DETAILED DESCRIPTION

The invention and accompanying drawings will now be discussed in reference to the numerals provided therein so as to enable one skilled in the art to practice the present invention. The drawings and descriptions are exemplary of various aspects of the invention and are not intended to narrow the scope of the appended claims.

The analysis of the PCD parts in the present application frequently discusses the pore length, pore size, or mean maximum pore length of the interstitial solvent metal pores. The mean maximum pore length or pore size is determined as follows. On an SEM or other suitable microscope with a scale marker capability multiple adjacent images of each exposed diamond layer are obtained. For each contained pore or region of solvent metal in these diamond layers the Pore Area and Feret's Diameter are determined. The Feret's Diameter is the longest continuous linear distance between any two points along the pore's perimeter, otherwise known as the caliper length. A software program such as NIST ImageJ is often used to facilitate determining this measurement. The image threshold is typically adjusted in the software so that each image highlights only the pore area (the solvent metal). Additionally, pores with an area below 0.5 square microns may be omitted from the analysis in order to reduce noise in the analysis. Each image is then analyzed across the exposed surface layer by first summing the pore area for all the images in the diamond layer. The pores are then ranked by pore area, and a set of the pores is created which includes a sufficient number of the pores with the largest surface area pores in order to include 80% of the total pore area. The average pore area and average Feret's diameter is then determined for this set. The average Feret's diameter of this set of pores is defined as the "Mean Maximum Pore Length" and is often referred to herein as the pore size.

Early work in making diamond prosthetic joints, such as in making PCD femoral head prostheses, was accomplished using a CoCrMo alloy (particularly the alloy ASTM F-75) for the solvent metal. ASTM F-75 is an alloy that is itself biocompatible and is commonly used in metal orthopedic implants for items such as hip femoral head implants and knee femoral resurfacing implants. The composition of the F-75 CoCrMo alloy is Co-38-Cr-6Mo, which is 66% Co, 28% Cr, and 6% Mo on a weight basis. The diamond layers of the PCD parts were made with diamond powders and the F-75 solvent metal.

It has been unexpectedly discovered that the PCD prosthetic components made by using the F-75 alloy as the solvent metal suffered from reduced biological compatibility. F-75 solvent metal PCD components which were sintered in the press as known in the art were tested for ionic elution in Hank's solution at pH 6. As discussed herein, testing in Hank's solution involved immersing the PCD part in the solution to test for metal ion elution from the part. The solution was changed daily so that the measured values reflect the quantity of metal ions released from the part per day. The PCD components exhibited an ionic elution rate of 7 ppm/day on average. In contrast, conventional metallic femoral head implants made solely from the F-75 CoCrMo alloy exhibited an ionic elution rate of less than 0.1 ppm/day on average. The elution test data indicates that the resulting metals in the PCD part after sintering were not responding in the same manner as the regular alloy to the elution test. To the contrary, the PCD component eluted metal ions at a rate up to 70 times as fast as a solid F-75 metal component. Cobalt, in particular, was eluted from the PCD component. Detailed examination of the PCD microstructure revealed the reason for the elevated cobalt release in the Hank's solution.

FIG. 1 shows a micrograph of a PCD part which has been sintered with the F-75 CoCrMo alloy. The solvent metal 110 is displayed in light grey in the micrograph while the diamond particles 120 are displayed in black. The solvent metal 110 fills the spaces between the diamond 120. Various parts of the solvent metal 110 have been labeled with numerals to show the ratios of cobalt to chrome of these various places in the solvent metal 110. The F-75 CoCrMo powder used as a solvent metal feedstock had an initial cobalt to chrome ratio of 2.4. After the sintering process, the metal has segregated into multiple phases including a chromium-rich phase having a Co:Cr ratio less than 2.4 and a cobalt-rich phase having a Co:Cr ratio greater than 2.4. Areas with up to 20× more cobalt than chromium are present in the PCD. It is understood that the chromium protects the metal from corrosion by forming a stable surface film of metal oxide and thus inhibits the elution of metal ions during testing and during use in a patient. Without the protective chromium and its resulting oxide, the cobalt-rich phase is much more susceptible to breakdown in solution, thereby yielding the high ion levels seen in the elution testing.

Figure 2:
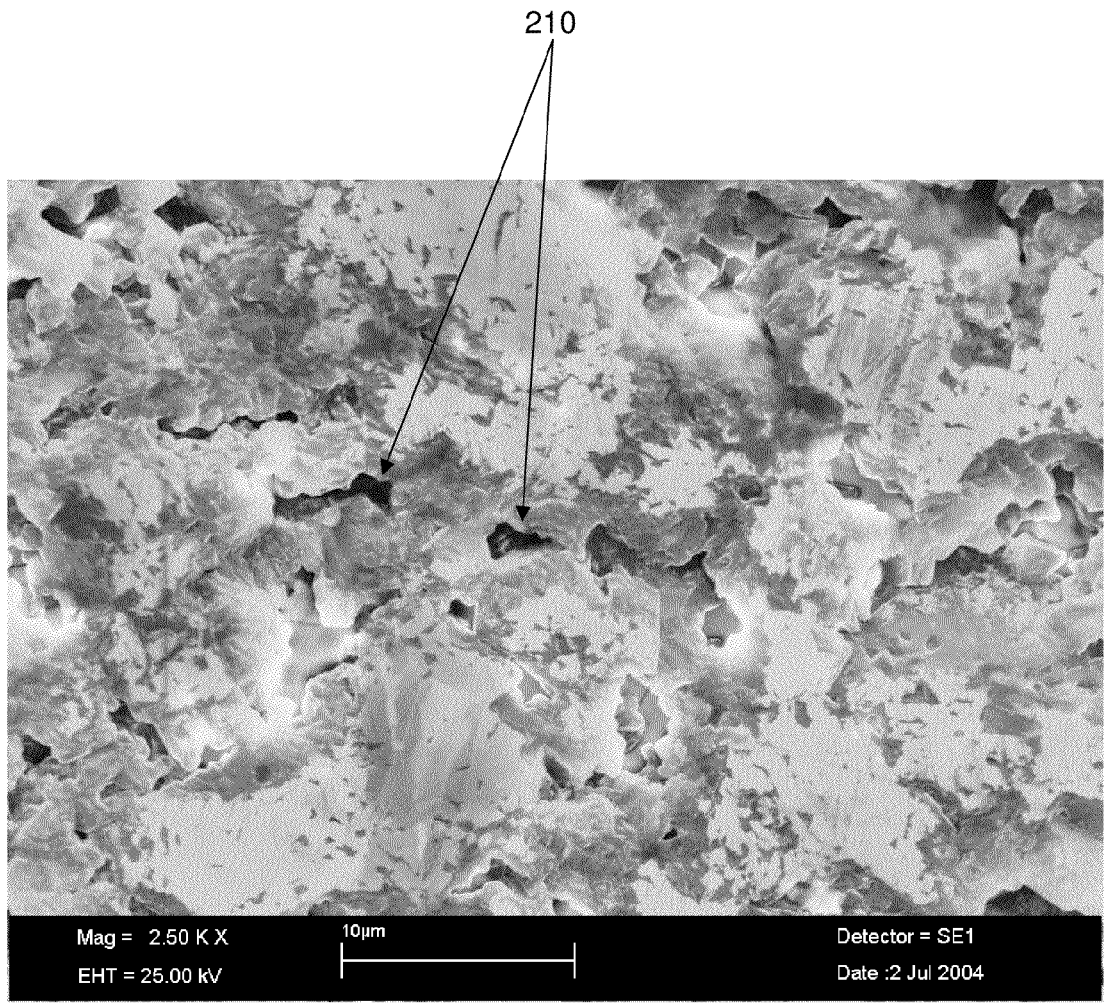
FIG. 2 shows a micrograph of a diamond layer of a PCD part which has been etched to remove the solvent metal.

It has been determined that the cobalt-rich areas often form filaments through the solvent metal material. This can be seen when the PCD part is etched in acid, as shown in FIG. 2. Etching the PCD part in a more acidic solution than the pH 6 Hank's solution would demonstrate a highly accelerated corrosion of the part. FIG. 2 clearly shows a network of 2 to 3 micron diameter holes 210 running though the PCD where the cobalt rich phase has been removed. The cobalt rich materials are rapidly removed, while the chromium-rich phases, which are more acid resistant (more resistant to corrosion), are left behind.

Several things may be observed from the testing and discovery discussed above. The composition of the solvent metal alloys used for sintering the diamond can change significantly during sintering of a PCD part. In particular, the solvent metal alloys may experience phase separation and carbide formation during sintering, leading to many different phases of metals or metal carbides in the resulting PCD part. Thus, metals which are ordinarily thought to be biologically compatible may not be biologically compatible if used as a solvent metal for sintering diamond. The changes to the solvent metal may result in excessive elution of metal ions from a PCD part placed in a biological environment, such as when implanted into a person, as demonstrated by the elution tests and acid etching tests.

Applicants initially believed that a general solution to this problem was to find a metal that is a stable oxide former that is not a strong carbide former, has a melting point in alloy form within an acceptable range for the high pressure process, and is biocompatible. One such proposed solution was the addition of tin (Sn) to the solvent metal in the PCD. Since tin is not a carbide former and has a relatively stable oxide, it was expected to stay alloyed with the main solvent metal and enhance its corrosion resistance. Tin is also neutral to diamond synthesis, so alloys can be found that provide acceptable diamond sintering.

While the addition of tin was initially thought to be a general solution, it was discovered that few combinations of tin and the other solvent metals active in diamond sintering and synthesis yield a solvent metal that will make appropriate PCD for medical implant applications. There are various reasons for this. One reason is that tin does not contribute to diamond synthesis. Tin does not hold much carbon in solution during sintering conditions, and therefore solvent metal alloys with tin have been found to decrease the amount of carbon available to the diamond grains during the PCD synthesis sintering reaction. The end result can be PCD that is not as well sintered. This decreases both the mechanical strength of the PCD as well as its wear and abrasion resistance. Experimental examples of various solvent metal compositions which include Sn are shown and described below.

Experiment SB53.1 used a sintering metal alloy (solvent metal) composed of 55% Sn and 45% Co. This mixture has a very slight (2.3%) excess of Co in relation to the $Co_3Sn_2$ phase, which should be advantageous since cobalt is the element that allows sintering. The solvent metal was used to create spherical femoral head components consisting of an outer layer of diamond, an inner gradient layer of diamond, a refractory metal layer, and a substrate. The outer layer was composed of 80% diamond and 20% solvent metal by weight, with the diamond being a mixture of 75% 20 micron diamond crystals and 25% 4 to 8 micron diamond crystals. The inner layer was composed of 50% 40 micron diamond crystals and 50% solvent metal. The inner layer solvent metal was 66% Co, 28% Cr, and 6% Mo by weight.

These parts were processed across a wide range of press sintering conditions (power, time, and pressure). None of the parts achieved sufficient sintering quality as determined by a grind resistance test. None of the parts exhibited grind resistance close to historical levels of parts that were sintered with straight CoCrMo in both layers, even though the inner layer was composed completely of CoCrMo and solvent metal is swept from the inner layer into the outer layer. The CoSn sintered parts ground away faster, indicating that the diamond was not as well bonded. The grind resistance of the part was determined by the rate that diamond is removed from the surface (or alternatively the time it takes to remove a set amount of diamond), the back pressure of the wheel during grinding (how much pressure is required to remove diamond), and the finish achieved by the grinding operation.

Experiment SB53.2 consisted of making spherical femoral head components having of an outer layer of diamond, an inner gradient layer of diamond, a refractory metal layer, and a substrate. The solvent metal was composed of 50% Sn and 50% Co. This mixture has a 7% excess of Co relative to $Co_3Sn_2$, which is expected to aid sintering quality. The outer layer was composed of 80% diamond and 20% solvent metal by weight, the diamond being a mixture of 75% 20 micron diamond crystals and 25% 4 to 8 micron diamond crystals. The inner layer was composed of 50% 40 micron diamond and 50% solvent metal. The inner layer solvent metal was 66% Co, 28% Cr, and 6% Mo by weight.

These parts were processed across a wide range of press sintering conditions (power, time, and pressure). None of the parts achieved sufficient sintering quality as determined by a grind resistance test. That is to say that none of the parts exhibited grind resistance which was close to that which is achieved in parts that were sintered using a CoCrMo alloy as the solvent metal in both of the diamond layers, even though the inner layer was composed completely of CoCrMo and solvent metal is swept from the inner layer into the outer layer.

Experiment SB50.3 consisted of making spherical femoral head components having of an outer layer of diamond, an inner gradient layer of diamond, a refractory metal layer, and a substrate. The solvent metal was composed of 45% Sn and 55% Co. This mixture has a 12% excess of Co relative to $Co_3Sn_2$, which should aid sintering quality. The outer layer was composed of 80% diamond and 20% solvent metal by weight. The diamond was a mixture of 75% 20 micron diamond crystals and 25% 4 to 8 micron diamond crystals. The inner layer was composed of 60% 40 micron diamond crystals and 40% solvent metal. The solvent metal was 66% Co, 28% Cr, and 6% Mo by weight.

These parts were processed across a wide range of press sintering conditions (power, time, and pressure). None of the parts achieved sufficient sintering quality as determined by a grind resistance test. None of the parts exhibited grind resistance close to historical levels of parts that were sintered with straight CoCrMo in both layers, even though the inner layer was composed completely of CoCrMo and solvent metal is swept from the inner layer into the outer layer.

Greatly increasing the Co level will eventually leave areas of Co that are not well alloyed with Sn and therefore less protected from corrosion and ion release. It is thus observed that the solvent metal containing just Sn and Co does not sinter well. It is currently believed that this is because the metal does not dissolve enough carbon into the metal solution to allow the diamond to sinter as well as it should.

In order to improve the sintering of the diamond crystals, the inventors determined that elements which increase the amount of carbon available to the reaction, or that are generally beneficial to sintering must be added. Two elements which were used are Mn and W. It has been determined that the addition of small amounts of these elements generally improve sintering of PCD. The negative side effect of these elements is that they both form compounds within the sintered PCD that are not very corrosion resistant, and thus these elements are more likely to pose corrosion problems.

Examples of experiments run with Mn and W in the solvent metal are detailed below.

Experiment SB58.1 consisted of making spherical femoral head components having of an outer layer of diamond, an inner gradient layer of diamond, a refractory can, and a substrate. The outer layer solvent metal was composed of 50% Sn and 40% Co and 10% Mn by weight. The outer layer was composed of 80% diamond and 20% solvent metal by weight. The diamond mix was 75% 20 micron diamond crystals and 25% 4 to 8 micron diamond crystals. The inner layer was composed of 50% 40 micron diamond crystals and 50% solvent metal. The inner layer solvent metal was 66% Co, 28% Cr, and 6% Mo by weight.

These parts were processed across a wide range of press sintering conditions (power, time, and pressure). The parts sintered easily and adequately as determined by a grind resistance test. All of the parts exhibited grind resistance equal to historical levels of parts that were sintered with straight CoCrMo in both layers.

Experiment SB59.1 consisted of making spherical femoral head components having of an outer layer of diamond, an inner gradient layer of diamond, a refractory metal layer, and a substrate. The outer layer solvent metal was composed of 50% Sn and 40% Co and 10% W by weight. The outer layer was composed of 80% diamond and 20% solvent metal by weight. The diamond was a mixture of 75% 20 micron diamond crystals and 25% 4 to 8 micron diamond crystals. The inner layer was composed of 50% 40 micron diamond crystals and 50% solvent metal. The inner layer solvent metal was 66% Co, 28% Cr, and 6% Mo by weight.

These parts were processed across a wide range of press sintering conditions (power, time, and pressure). The parts sintered easily and adequately as determined by a grind resistance test. All of the parts exhibited grind resistance equal to historical levels of parts that were sintered with straight CoCrMo in both layers.

Elution testing of these two components showed continued release of both Mn and W over time in the Hank's solution. The average daily elution rate in pH 6 Hank's solution was 1.91 ppm for Mn and 0.06 ppm for W. Mn and W are not biocompatible ions and are problematic for biocompatibility, even at low levels. These experiments demonstrate that while other elements may be added to increase sintering quality, not all combinations will yield results that have acceptable biocompatibility.

Applicants thus discovered that another element should be substituted for Mn or W that can assist in sintering and form a stable end reaction product that does not come off in elution. In this case, Cr and Mo can be added to the solvent metal to assist sintering if Sn is present in the correct amount to protect the Co. Both Cr and Mo form stable carbides, often mixed together, that are stable in physiologic environments, so neither element comes off in elution.

Figure 5A:
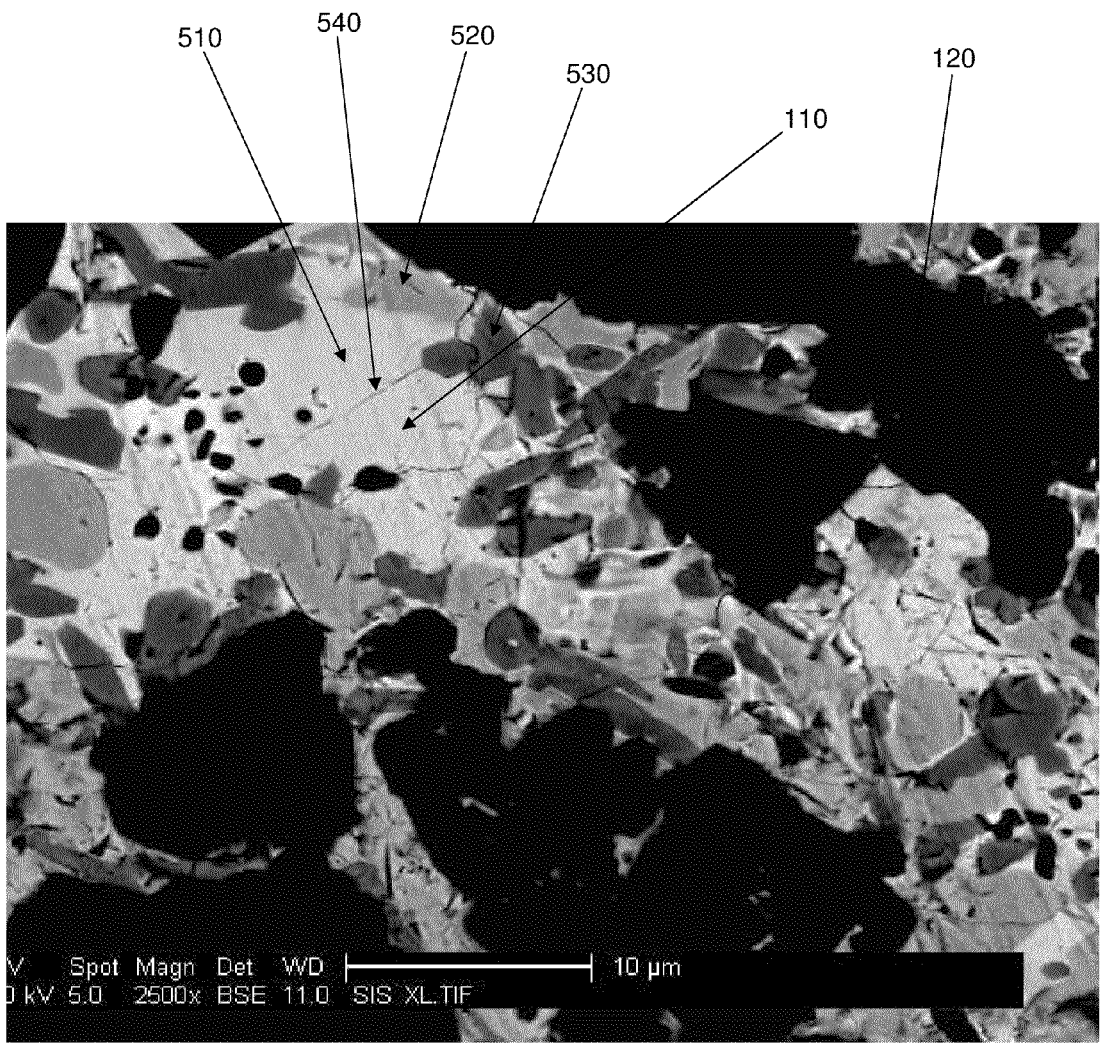
FIG. 5a shows a micrograph of a diamond layer of a PCD part.

Diamond synthesis conditions are such that the input metal constituents of the solvent metal react in unexpected ways. For instance, Co, Sn, and Cr in the solvent metal feedstock will primarily form two phases during sintering which are then present in the solvent metal 110. These can be seen in FIG. 5a. The first phase 510 is composed of approximately 59% Sn and 39% Co and 2% Cr by weight. The second phase 520 is approximately 50% Co, 42% Sn, and 8% Cr by weight. The ratio of the phases formed from any feedstock material is not easily predictable solely on the basis of amount of each constituent alloy. Other constituents, such as Cr and Mo generally form carbides, often together. A mixed carbide 530 is commonly formed from alloys that contain both Cr and Mo is 70% Cr, 15% Mo, and 15% C by weight. It is thus not typically possible to predict ahead of time what the exact ending composition of any feedstock solvent metal combination will be. The ending composition of the solvent metal typically includes metal carbides and separated metal phases of varying composition. The ending condition is of course critical to the corrosion resistance and biocompatibility of the PCD, but is not predictable from the starting composition.

Experiment SB063.1 consisted of making spherical femoral head components having an outer layer of diamond, an inner gradient layer of diamond, a refractory metal layer, and a substrate. The outer layer solvent metal was composed of 50% Sn and 40% Co and 10% Cr by weight. The outer layer was composed of 80% diamond and 20% solvent metal by weight. The diamond was a mixture of 75% 20 micron diamond crystals and 25% 4 to 8 micron diamond crystals. The mean maximum pore length of the outer layer was approximately 5 microns. The inner layer was composed of 50% 40 micron diamond crystals and 50% solvent metal. The solvent metal was 66% Co, 28% Cr, and 6% Mo by weight.

These parts were processed across a wide range of press sintering conditions (power, time, and pressure). The parts sintered easily and adequately as determined by a grind resistance test. All of the parts exhibited grind resistance equal to historical levels of parts that were sintered with CoCrMo solvent metal in both layers. The outer surface of the parts were tested by elution in Hank's Solution at pH6. The average cobalt ion release of this series over 4 days was 1.93 ppm, 1.12 ppm, 1.05 ppm, and 1.05 ppm. No Cr or Sn ions were detected.

SB050.1 consisted of making spherical femoral head components having an outer layer of diamond, an inner gradient layer of diamond, a refractory metal layer, and a substrate. The outer layer solvent metal was composed of 33% Sn and 44.2% Co and 18.8% Cr and 4% Mo by weight. The outer layer was composed of 80% diamond and 20% solvent metal by weight. The diamond was a mixture of 75% 20 micron diamond crystals and 25% 4 to 8 micron diamond crystals. The mean maximum pore length of the outer layer was approximately 5 microns. The inner layer was composed of 50% 40 micron diamond crystals and 50% solvent metal. The solvent metal was 66% Co, 28% Cr, and 6% Mo by weight.

These parts were processed across a wide range of press sintering conditions (power, time, and pressure). The parts sintered easily and adequately as determined by a grind resistance test. All of the parts exhibited grind resistance equal to historical levels of parts that were sintered with straight CoCrMo in both layers. The outer surface of the parts were tested in elution at pH6. The average cobalt ion release of this series over 5 days was 0.9 ppm, 0.61 ppm, 0.72 ppm, 0.96 ppm, and 0.83 ppm. No Mo, Cr or Sn ions were detected.

Experiment SB86.2.4 involved a femoral head with two diamond layers. The outer diamond layer contained 80% diamond by weight, with the diamond being 75% 20 micron diamond crystals and 25% 4 to 8 micron diamond crystals. The inner (gradient transition) diamond layer contained 40% diamond by weight, with 100% 40 micron diamond crystals. The solvent metal was the balance of the diamond layer composition by weight, and contained 46% Sn, 40% Co, 12% Cr, and 2% Mo. The exposed outer diamond layer of the PCD part was elution tested in a Hanks solution with the pH buffered to 6.0. Metal ion levels in the Hanks solution were monitored over five days to check for corrosion from the PCD part. Metal ion levels started at 0.58 ppm and declined to 0.37 ppm by the fifth day. This composition was determined to sinter well as it achieves both a high strength and grind resistance and also to have a very low elution of metal ions, indicating a very high degree of biocompatibility.

Additional testing of similar solvent metal alloy compositions determined that nominal changes to the composition of the SB86.2.4 test still achieved both adequate sintering and acceptable biocompatibility as measured by ionic elution. Such nominal changes to the composition included solvent metal compositions such as 46.5% Sn, 39.7% Co, 11.8% Cr, and 2% Mo by weight. Thus, a solvent metal composition of 46% Sn, 40% Co, 12% Cr, and 2% Mo plus or minus a few percent of each component achieved both adequate strength and grind resistance as well as very low metal ion elution. While the examples shown above (SB050.1 composed of 33% Sn and 44.2% Co and 18.8% Cr and 4% Mo and SB063.1 composed of 50% Sn and 40% Co and 10% Cr) had slightly higher elution of metal ions than the optimal solvent metal composition of SB86.2.4, they achieved significantly reduced elution of metal ions and thus improved biocompatibility over prior art compositions.

The above described solvent metal compositions which include Sn provide improved biocompatibility and increased corrosion resistance. The solvent metal compositions discussed have appropriate amounts of metal such that the resulting interstitial metals in the PCD after sintering are biocompatible and corrosion resistant. The composition of the interstitial metal in the PCD part typically differs from the initial solvent metal composition since some degree of carbide formation, phase separation, etc. will occur during sintering, but the resulting interstitial material is generally corrosion resistant and biocompatible. Additionally, the improved solvent metal compositions still sinter well and result in a PCD which has sufficient strength and grind resistance, and which will thus provide adequate mechanical performance as a prosthetic joint.

Pore Size Control

In addition to improving biocompatibility and corrosion resistance through new solvent metal compositions, it has also been discovered that improved biocompatibility can be achieved through control of the solvent metal pore size in the finished PCD part. As used herein, the term pore size refers to the size of the interstitial solvent metal pores between the particles of diamond in the PCD part (the interstitial solvent metal, typically comprising multiple phases of metals and even carbides formed during sintering). Thus, the pore size is often measured and discussed herein in micro meters. The interstitial solvent metal typically forms a network of veins through the diamond crystals, as is visible in many of the micrographs shown herein. It has been determined that when the width of the veins of solvent metal exceeds a certain width, micro cracks develop in the solvent metal. These micro cracks tend to accelerate corrosion and thus reduce biocompatibility.

Thus, biocompatibility and corrosion resistance may also be improved by controlling the maximum width or size of the veins of solvent metal which are exposed in the resulting PCD part. Reducing the width of the veins of solvent metal will significantly reduce or even eliminate the occurrence of micro cracking. It is believed that the micro cracking occurs due to the physical stresses present in the solvent metal caused by increased shrinkage of the solvent metal relative to the diamond particles during cooling of the PCD part. These stresses are believed to place the solvent metal in tension and cause micro cracks. It has further been discovered that improved solvent metal compositions which contain Sn, while being more corrosion resistant as a material after sintering, tend to exhibit increased micro cracking. Thus, the reduction in exposed pore size to thereby reduce micro cracking provides some improvement in biocompatibility for many solvent metal compositions and provides a significant improvement in biocompatibility for solvent metal compositions containing Sn. PCD parts made with both the improved solvent metal composition and the pore size control discussed herein provide a significant improvement in biocompatibility over previous PCD parts.

PCD prostheses are generally composed of a diamond table consisting of several layers, including gradient transition layers, and a suitable substrate. The composition of each layer must be tailored so that the Coefficient of Thermal Expansion (CTE) and dilatation are compatible with the adjacent layers in order to produce a balanced and strong construct. Thus, the intermediate (gradient) diamond layers are typically used to provide a more gradual transition between the substrate material and the outer diamond layer material. Gradient layers of diamond are generally used to provide a gradual transition in composition between the substrate and the outer diamond layer to reduce the stresses between each layer and provide a joint which is mechanically stable.

The outer layer or bearing layer of the part is composed of diamond crystals of a certain size range to achieve the performance goals of the part, such as wear resistance. This outer layer may typically have less metal content and smaller diamond grain size depending on its use. If the PCD part includes a substrate, a gradient interface layer of diamond may be used to increase the attachment strength of the PCD to the substrate and reduce interfacial stresses between the substrate and the outer diamond layer. This gradient layer may also provide a sweep source of solvent metal moves through the outer layer or layers of diamond and helps to conduct impurities out of the PCD. The gradient transition layer usually has a higher metal content and larger diamond grain sizes than the outer diamond layer. As a result, the gradient transition layer (or layers) typically has larger solvent metal pore sizes than the outer layer. In the case of the PCD prosthetic hip femoral head, for example, several diamond layers may be used which contain varying amounts of solvent metal and varying diamond grain sizes and thus have a variety of resulting solvent metal pore sizes.

Figure 3:
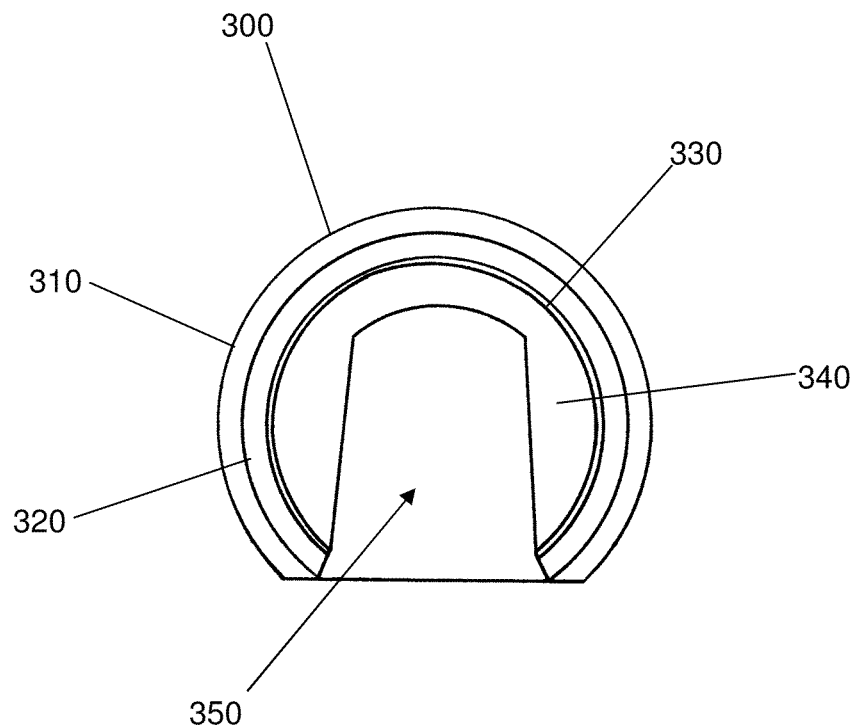
FIG. 3 shows a cross sectional view of an exemplary PCD prosthetic joint component.

FIG. 3 shows a cross sectional view of a PCD femoral head 300. The femoral head 300 is exemplary of the different elements of a PCD prosthetic joint part. It will be appreciated that the present invention is not limited only to femoral heads, but applies equally to other prosthetic joint parts made of PCD such as prosthetic spinal discs, etc. It is also appreciated that a prosthetic joint typically involves two mating components, such as the femoral head 300 and the mating socket (not shown for clarity). The socket would typically include the same structures as the femoral head 300, including a substrate, refractory metal can, gradient transition layers, and a bearing surface layer as discussed herein. The femoral head 300 includes an outer diamond layer 310 that forms the bearing surface, an inner layer of diamond that forms the gradient transition layer 320, a Nb refractory can 330, and a substrate 340. Additional gradient transition layers 320 may be used if desired, but a single layer is shown for clarity. The refractory can 330 is often made from a metal such as Nb, and although not always necessary, may be used to form a barrier between the substrate 340 and the diamond layers 310, 320 so that metals from the substrate do not flow through the diamond layers.

A morse taper socket 350 is typically formed in the femoral head 300 for attachment to a femoral hip stem. It is seen how the socket 350 cuts through each diamond layer 310 and 320. As such, each layer of the femoral head 300 must be biologically compatible and corrosion resistant, rather that merely the outer layer being biologically compatible and corrosion resistant.

Figure 4:
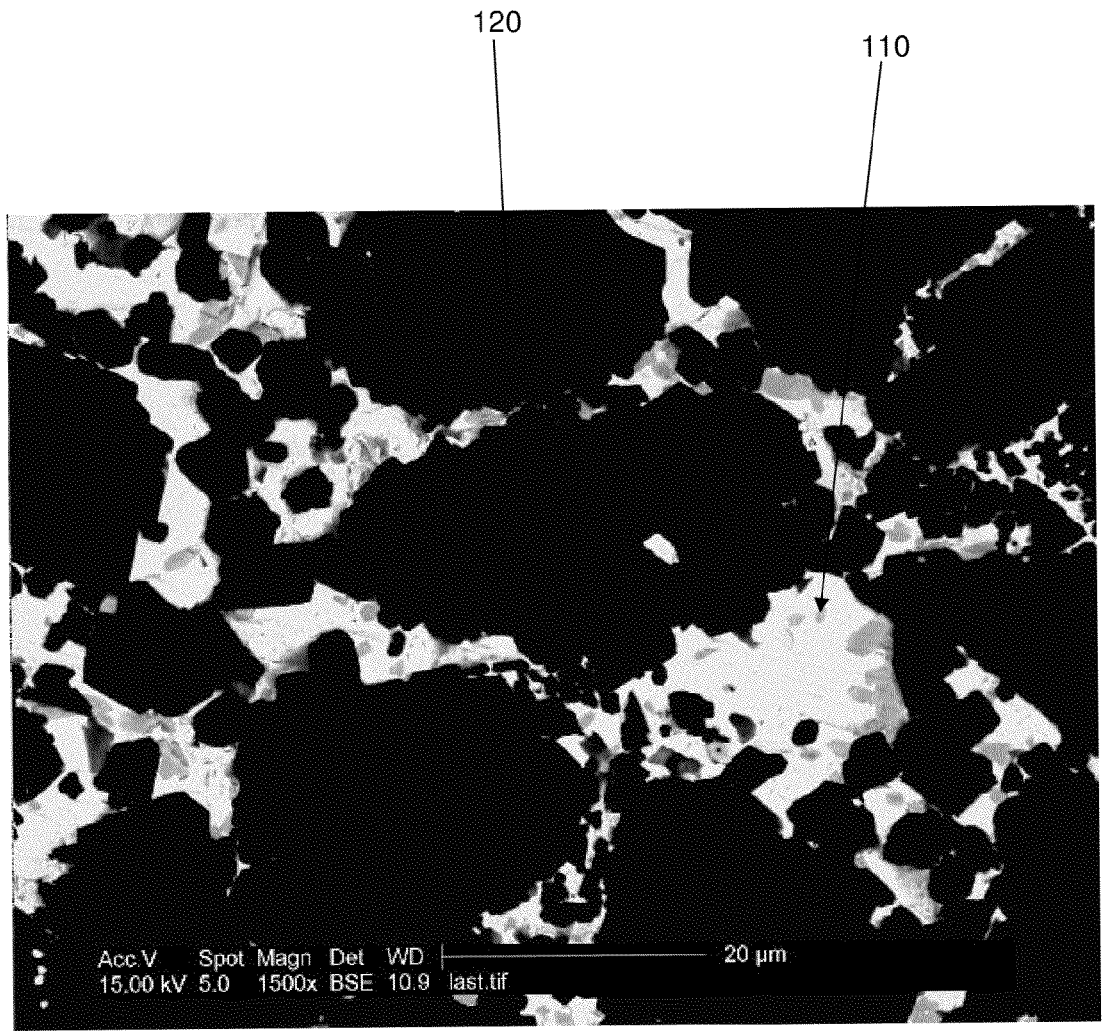
FIG. 4 shows a micrograph of a diamond layer of a PCD part.

FIG. 4 shows a micrograph which illustrates the solvent metal 110 that is located in the interstices or pores of a diamond matrix 120, such as the diamond layers of the prosthetic joint component 300. These interstitial spaces, or pores within the diamond, vary in size depending on the diamond to metal ratio as well as upon the various sizes of the diamond grains that make up the diamond content.

Gradient layers nearest the substrate are preferentially formed with higher metal to diamond content compared to the surface or bearing layer of PCD. The ratio of diamond to metal in a transitional diamond layer provides the correct CTE and dilatation for a proper bond with both the substrate and the adjacent diamond layer. The transitional layer typically is configured to have a CTE and dilatation which is intermediate to that of the adjacent layers and thereby reduce interface stress between these layers. Inner transitional diamond layers are also typically formed from larger sized diamond crystals than in the outer layers so that the diamond crystals contact each other and form a lattice of connected diamond crystals during sintering despite the elevated metal content. In most PCD devices, the diamond bearing layers will be cut in some location, exposing these inner layers. For example, the taper 350 in the femoral head of FIG. 3 is made by cutting through the different diamond layers 310 and 320 as well as the substrate material 340. Prosthetic joint components are thus often cut in order to properly size the component or to provide mounting structures, exposing the inner diamond layers.

Figure 5B:
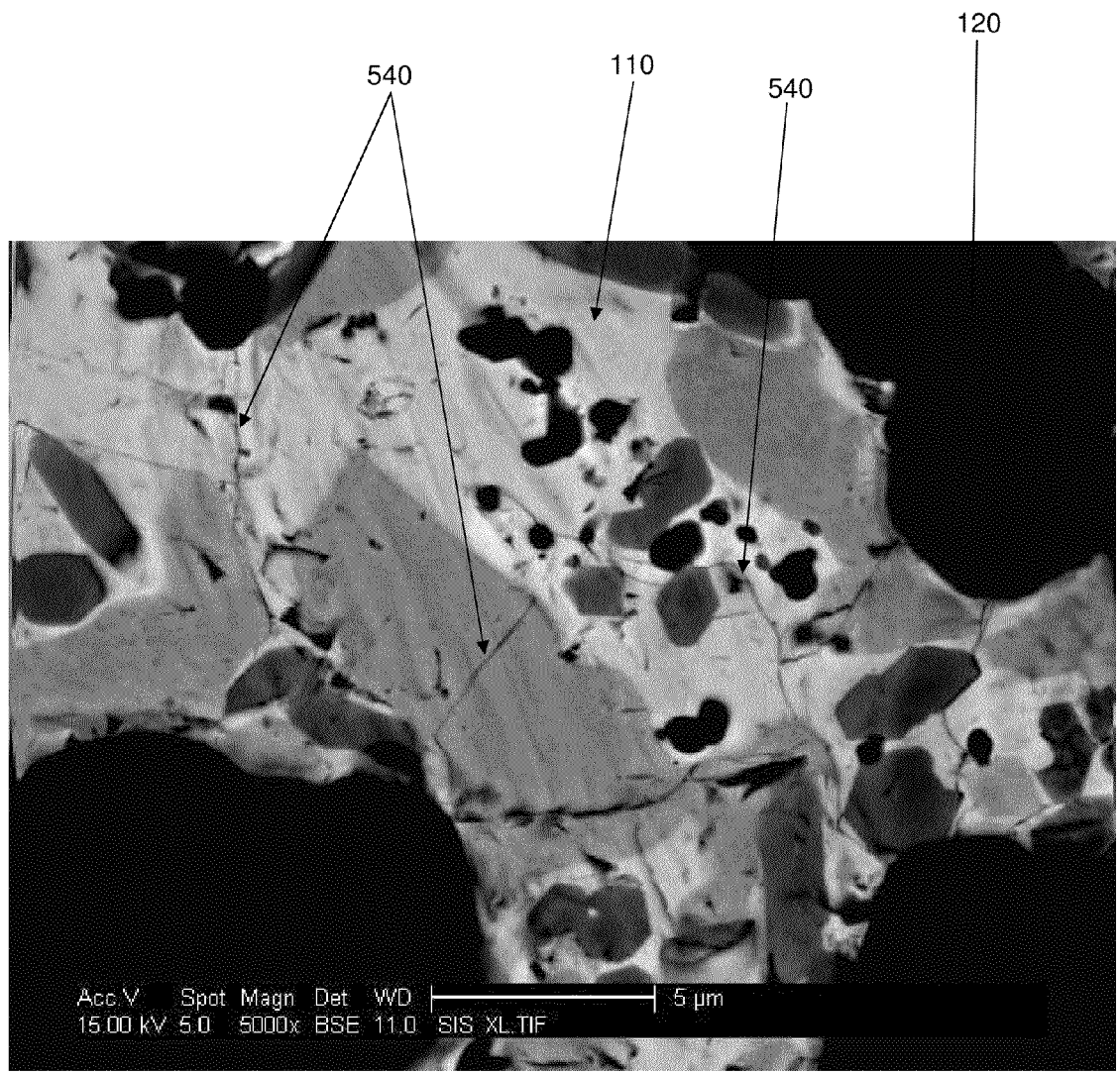
FIG. 5b shows a micrograph of a diamond layer of a PCD part.

The present invention thus provides for the control of the size of the metal pores in each of the diamond layers such as the gradient transition layers of diamond so as to provide for a reduction in the size of the metal pores on the exposed PCD surfaces. As is presently understood, the PCD part undergoes various changes during parts of the sintering process. During the sintering process, the diamond crystals bond to each other and form a scaffold of relatively fixed size. When the pressure and temperature are released from the high pressure and temperature cell, the diamond changes volume relatively little. This is because diamond has a coefficient of thermal expansion of 1.1 ($10^{-6}$/Deg C.) which is among the lowest of any known material and a Young's modulus of 1.22 GPa, which is among the highest. At the same time, the solvent metal must go from a liquid state to a solid state. Metals loose volume both as a function of cooling in each physical state and during the transition from liquid to solid. Sn, for example, has a density of 6.99 g/cc as a liquid and 7.265 g/cc as a solid. The solvent metal is contained in the pores of the PCD, which have a relatively fixed size because of the rigidity of the diamond crystal structure. Since the liquid sintering metal is freezing within this fixed volume, contraction cracking (or solidification cracking) of the solvent metal may result, especially in the larger pores. These micro cracks 540 can be seen in FIGS. 5a and 5b. These areas of micro cracking 540 within the solvent metal create a crevice environment and lead to crevice corrosion within the alloy.

The mechanism of increased corrosion in crevice environments is understood to include a combination of oxidation and limited diffusion. In short, in an aqueous environment, water molecules react with the metal surface through oxidation and other pathways. In oxidation, the oxygen atom is removed from water leaving the two hydrogen atoms as H+ ions. In a crevice environment, there is insufficient diffusion to allow the H+ ions to escape from the crevice or more oxygen to diffuse in to react with the H+, so the pH in the crevice goes down (the liquid becomes more acidic). This in turn leads to an acceleration of corrosion within the crevice and an even lower pH as more H+ ions are released.

Previously, it was not understood that solidification micro cracking occurred in the solvent metal veins. It was therefore not recognized that these micro cracks contributed significantly to the overall corrosion of the PCD part and the release of metal ions from the part, thereby reducing the biocompatibility of the part. As such, the composition of the inner gradient diamond layers was selected to bridge the coefficient of thermal expansion and dilation differences between the substrate and the outer diamond layer which was mostly diamond so as to present a very high wear resistance. These inner gradient layers thus had elevated metal content and consisted of large diamond crystals so that the diamond crystals would contact each other during sintering to increase the mechanical strength of the PCD part.

Applicants have discovered that to keep the solidification cracking to a level that does not effect the biocompatibility performance of PCD, i.e. gives adequate biocompatibility performance, the size of the solvent metal pores between diamond crystals must be maintained below a certain critical size. The size of the solvent metal pores is defined and discussed herein as the Mean Maximum Pore Length, or more simply as the pore size. The present invention uses multiple sizes of diamond crystals including smaller diamond crystals in the inner diamond layers in order to reduce the pore size while maintaining the use of larger diamond crystals so that the diamond crystals still bond to each other during sintering and provide a more stable interconnected construct.

The Mean Maximum Pore Length or pore size is determined as follows. On an SEM or other suitable microscope with a scale marker capability multiple adjacent images of each exposed diamond layer are obtained. For each contained pore or region of solvent metal in these diamond layers the Pore Area and Feret's Diameter are determined. The Feret's Diameter is the longest continuous linear distance between any two points along the pore's perimeter, otherwise known as the caliper length. A software program such as NIST ImageJ is often used to facilitate determining this measurement. The image threshold is typically adjusted in the software so that each image highlights only the pore area (the solvent metal). Additionally, pores with an area below 0.5 square microns may be omitted from the analysis in order to reduce noise in the analysis. Each image is then analyzed across the exposed surface layer by first summing the pore area for all the images in the diamond layer. The pores are then ranked by pore area, and a set of the pores is created which includes a sufficient number of the pores with the largest surface area pores in order to include 80% of the total pore area. The average pore area and average Feret's diameter is then determined for this set. The average Feret's diameter of this set of pores is defined as the "Mean Maximum Pore Length" and is often referred to herein as the pore size.

The following experiments were conducted in order to determine compositions for the transitional diamond layers and the bearing surface diamond layer and to determine pore sizes which substantially eliminate micro cracking and thereby improve the biocompatibility of the resulting PCD part. PCD Femoral head implants were fabricated containing several layers of diamond and solvent metal surrounding a substrate, such as is illustrated in FIG. 3. A number of those experiments are presented herein to demonstrate the effect of various diamond crystal sizes and resulting pore sizes.

Figure 6A:
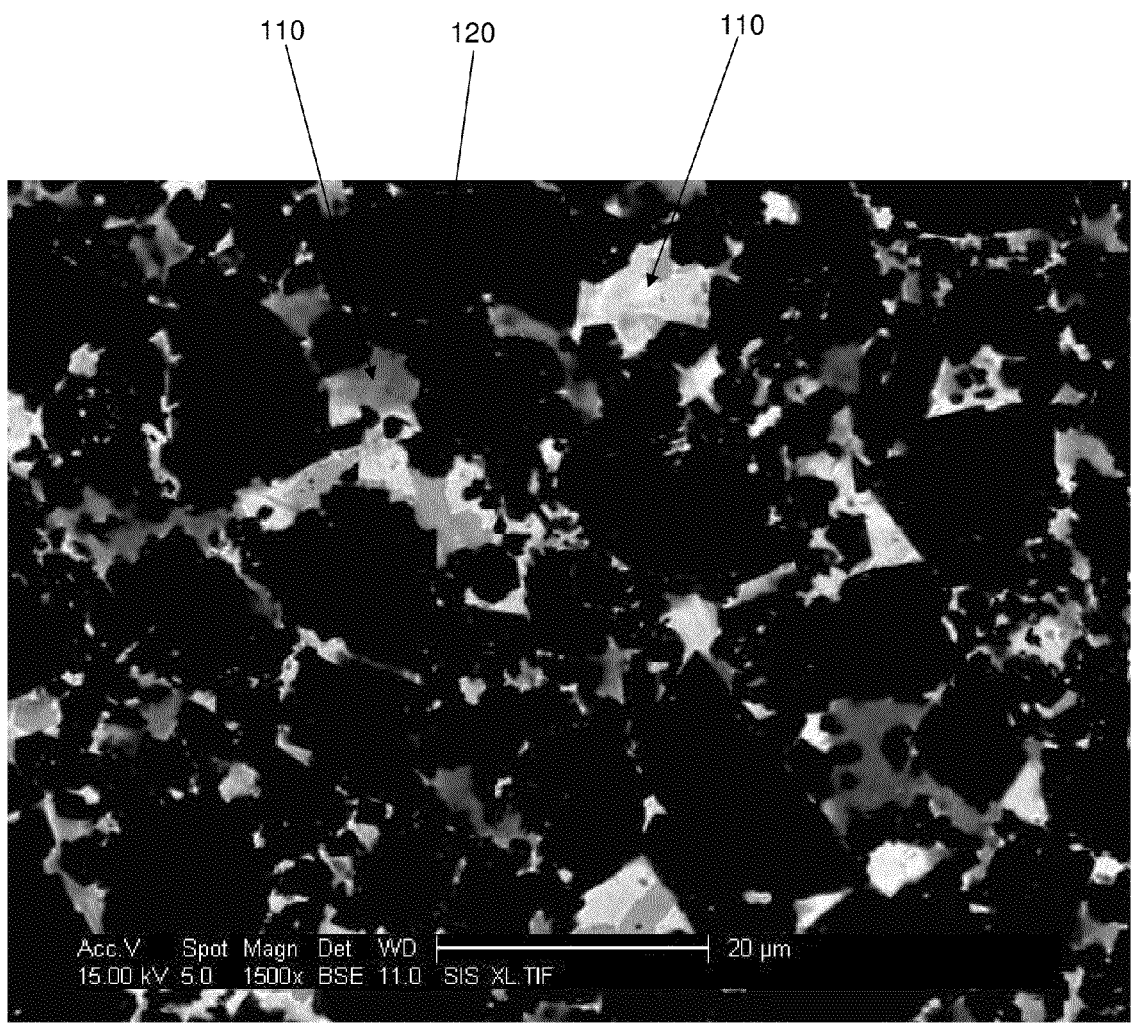
FIG. 6a shows a micrograph of a diamond layer of a PCD part.
Figure 6B:
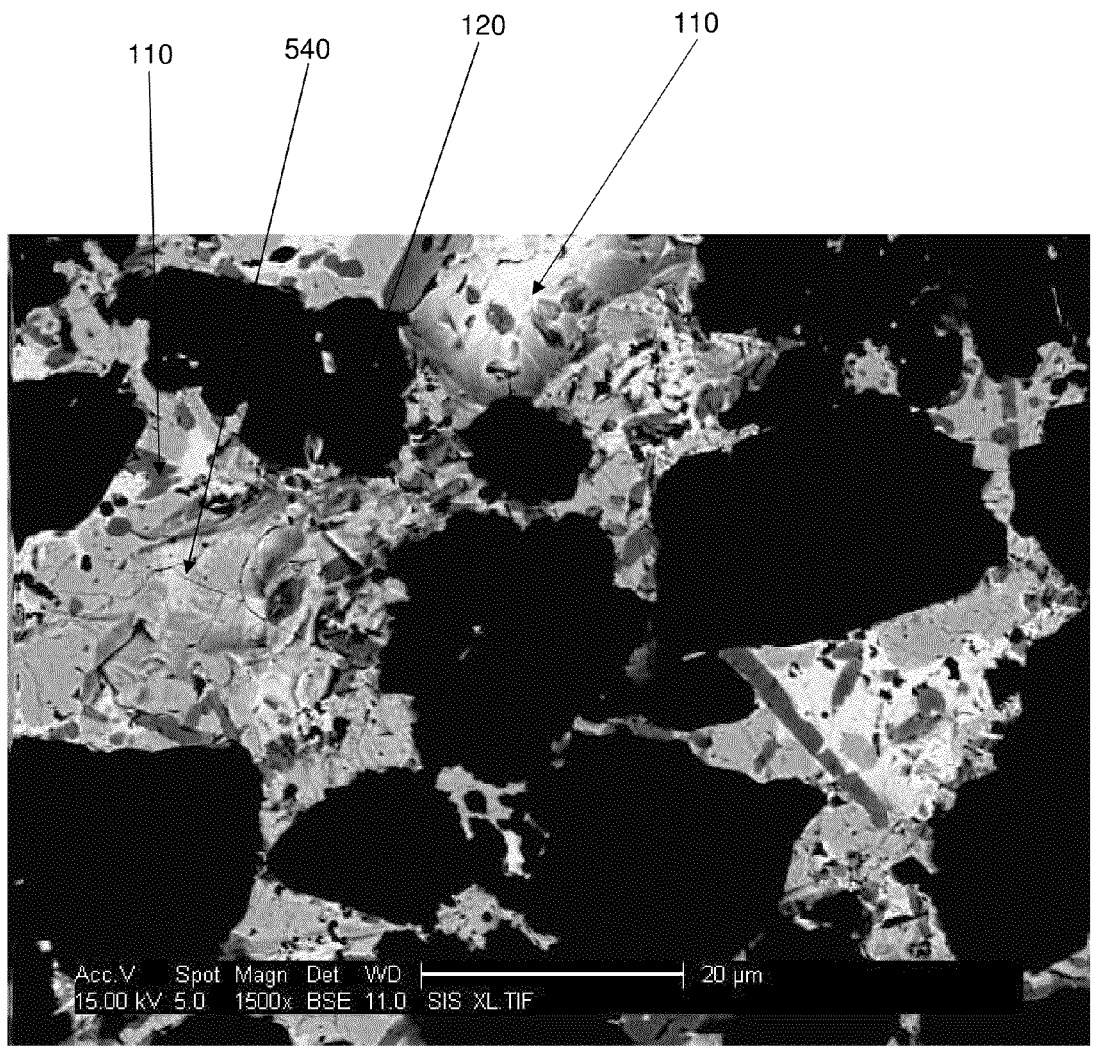
FIG. 6b shows a micrograph of a diamond layer of a PCD part.

Experiment SB86.2.4 involved a femoral head with two diamond layers. The outer diamond layer contained 80% diamond by weight, with the diamond being 75% 20 micron diamond crystals and 25% 4 to 8 micron diamond crystals. The inner (gradient transition) diamond layer contained 40% diamond by weight, with 100% 40 micron diamond crystals. The solvent metal was the balance of the diamond layer composition by weight, and contained 46% Sn, 40% Co, 12% Cr, and 2% Mo. FIG. 6a shows a micrograph of the outer diamond layer, illustrating the solvent metal pores 110 and the diamond matrix 120. The outer diamond layer was analyzed as discussed above, and had a mean maximum pore length of 4.95 microns. FIG. 6b shows a micrograph of the inner gradient diamond layer. The inner layer was analyzed as discussed above and had a mean maximum pore length of 54.79 microns.

The exposed outer diamond layer of the PCD part was elution tested in a Hanks solution with the pH buffered to 6.0. Metal ion levels in the Hanks solution were monitored over five days to check for corrosion from the PCD part. Metal ion levels started at 0.58 ppm and declined to 0.37 ppm by the fifth day. The PCD part was then cut to expose the inner layer and substrate and was retested for five days for corrosion in a similar Hanks solution. Metal ion levels in the Hanks solution started at 7.2 ppm and increased to 7.8 ppm by the fifth day. The micrographs of the inner layer illustrated in FIG. 6b show that the large solvent metal pores 110 present in the inner layer exhibited micro cracks 540. As the solvent metal composition of the outer diamond layer and inner diamond layer is the same, the elution testing test demonstrates the effect of large pore size and micro cracks on corrosion and the elution of metal ions from the PCD part.

Experiment SB87.3.1 involved a series of PCD femoral head parts which had three diamond layers. The outer diamond bearing layer containing 80% diamond by weight, having a mixture of 75% 20 micron diamond crystals and 25% 4 to 8 micron diamond crystals. The middle diamond layer contained 60% diamond by weight, the diamond being a mixture of 50% 40 micron diamond crystals, 38% 20 micron diamond crystals, and 12% 4 to 8 micron diamond crystals. The inner diamond layer contained 40% diamond by weight, the diamond being 100% 40 micron diamond crystals. The solvent metal constituted the balance of these layers, and consisted of 46% Sn, 40% Co, 12% Cr, and 2% Mo. The parts were cut to expose all layers of the PCD. Micrographs of the outer, middle, and inner diamond layers can be seen in FIGS. 7a, 7b, and 7c respectively, illustrating the solvent metal pores 110 and the diamond crystals 120.

Figure 7A:
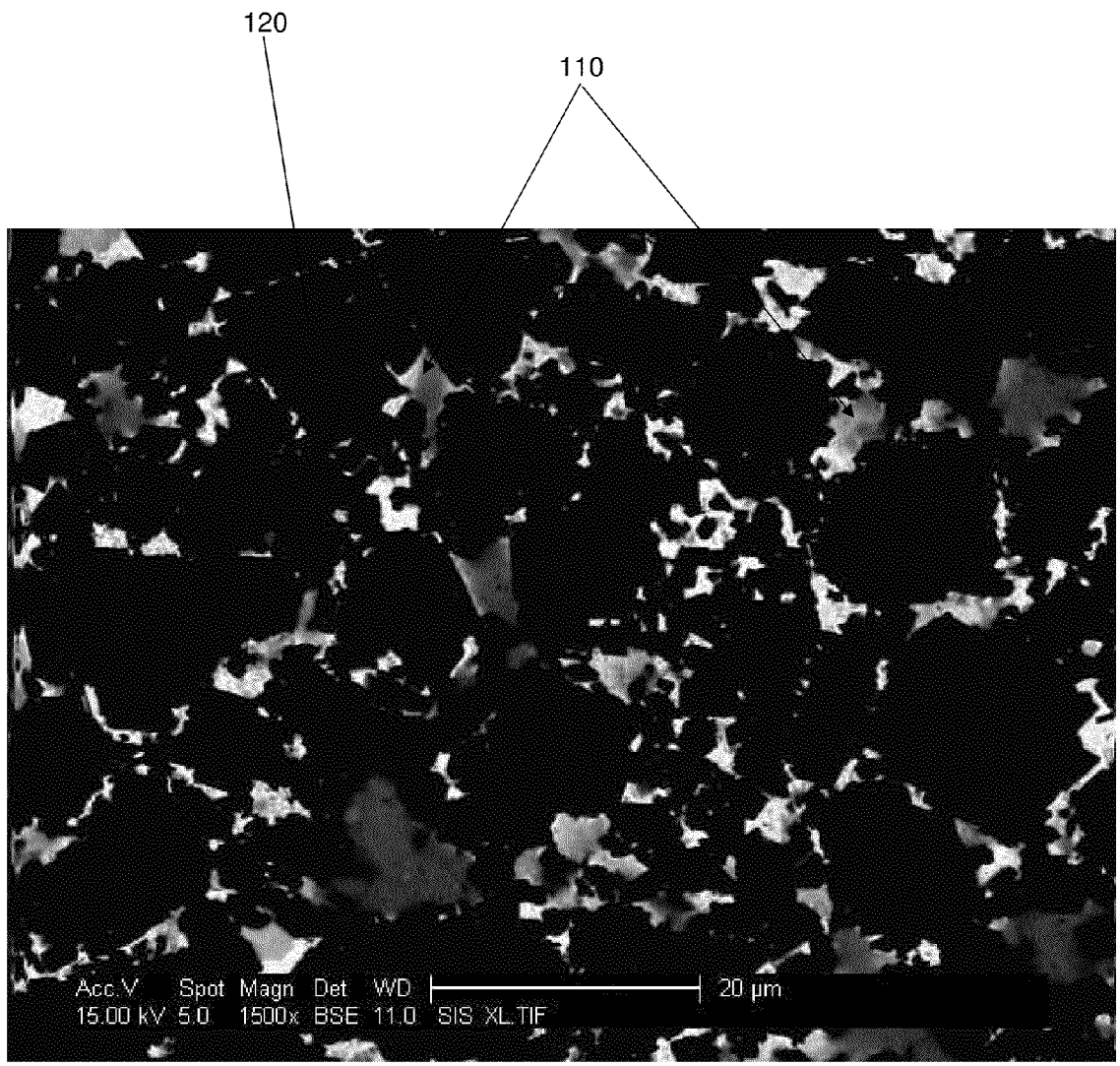
FIG. 7a shows a micrograph of a diamond layer of a PCD part.
Figure 7B:
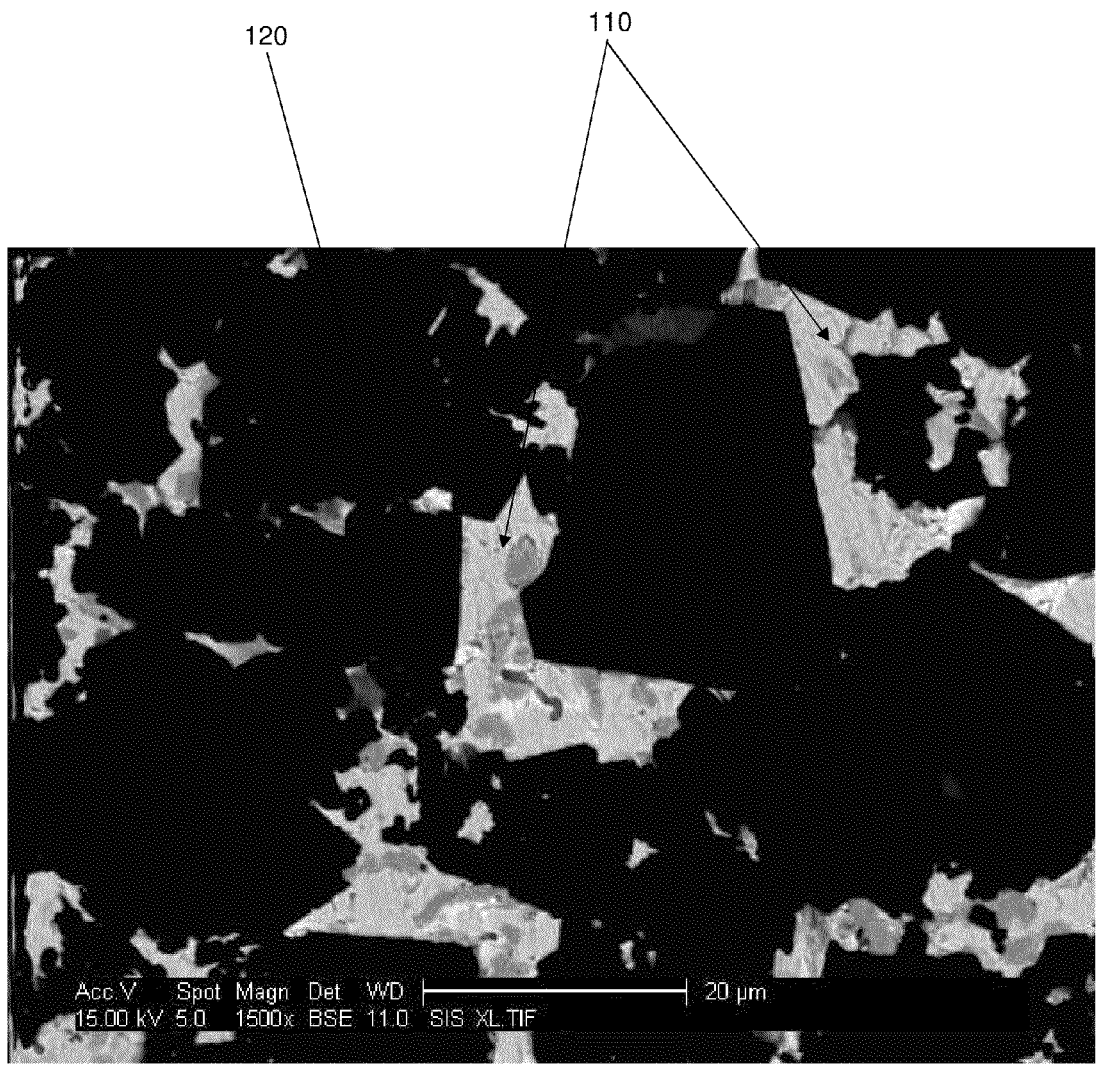
FIG. 7b shows a micrograph of a diamond layer of a PCD part.
Figure 7C:
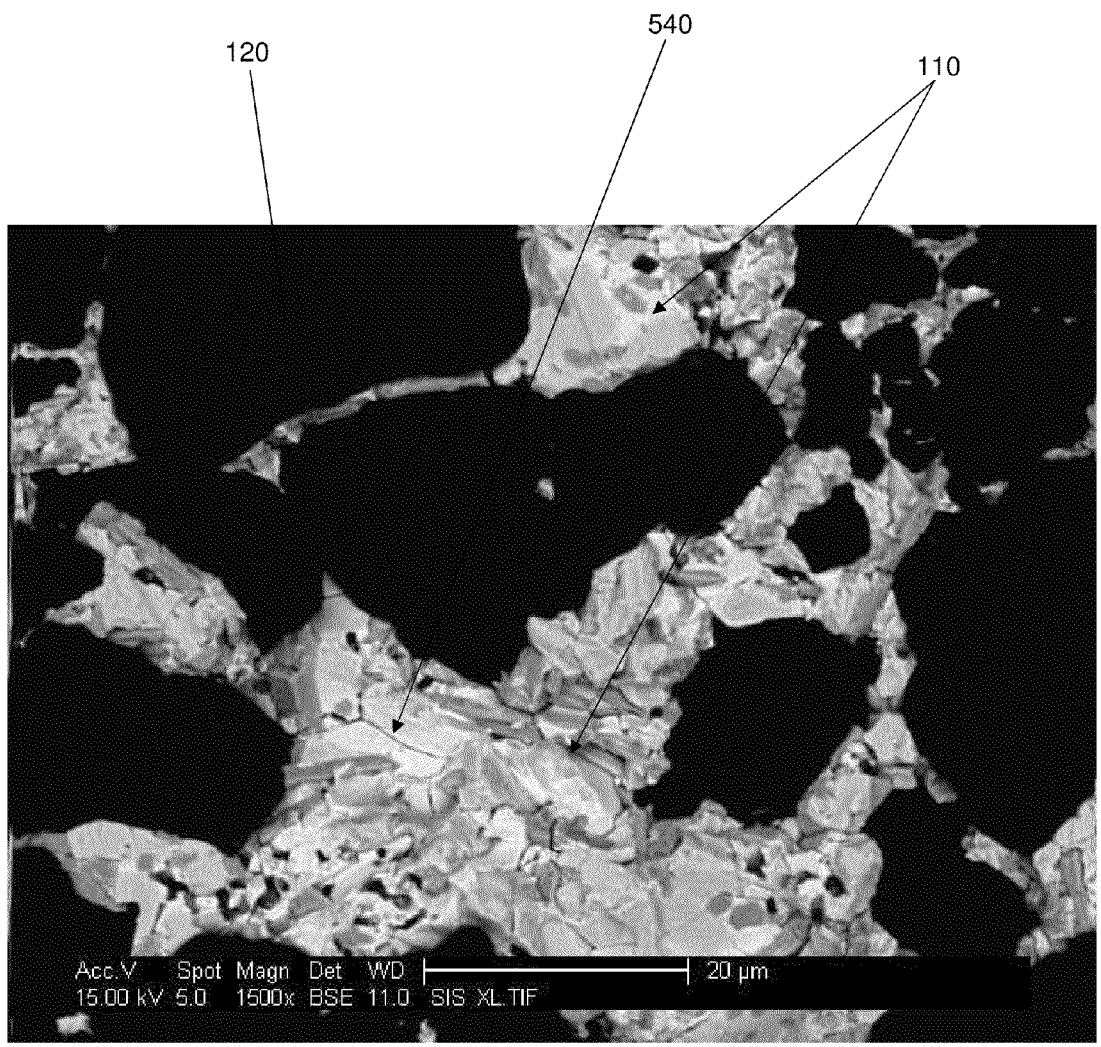
FIG. 7c shows a micrograph of a diamond layer of a PCD part.

The outer layer, shown in FIG. 7a, had a mean maximum pore length of 5.63 microns. The middle layer shown in FIG. 7b had a mean maximum pore length of 14.3 microns. The inner layer shown in FIG. 7c had a mean maximum pore length of 35.48 microns. The PCD parts were tested in Hanks solution elution tests with the pH buffered to 6.0. Average ion levels in the Hanks solution over five days were 5.9 ppm, 5.75 ppm, 6.05 ppm, 5.95 ppm, and 5.2 ppm respectively. Solidification cracks 540 may be observed in FIG. 7c. It is understood that the solidification cracks 540 in large solvent metal pores contributes to increased corrosion and the elevated release of metal ions. The increased elution of metal ions is of particular concern because these are heavy metal ions which are toxic.

Another experimental series of PCD femoral heads, SB 105.1.1, was similar to SB87.3.1 but had a lower average maximum pore length in the inner layer. The PCD parts again had three diamond layers. The outer diamond layer contained 80% diamond by weight, the diamond being a mixture of 75% 20 micron diamond crystals and 25% 4 to 8 micron diamond crystals. The middle layer contained 50% diamond by weight with the diamond being a mixture of 50% 40 micron diamond crystals, 38% 20 micron diamond crystals, and 12% 4 to 8 micron diamond crystals. The inner layer contained 40% diamond by weight with the diamond being a mixture of 65% 20 micron diamond crystals, 15% 10 micron diamond crystals, and 20% 4 to 8 micron diamond crystals. The solvent metal formed the balance of the three diamond layers, and consisted of 46% Sn, 40% Co, 12% Cr, and 2% Mo.

Figure 8A:
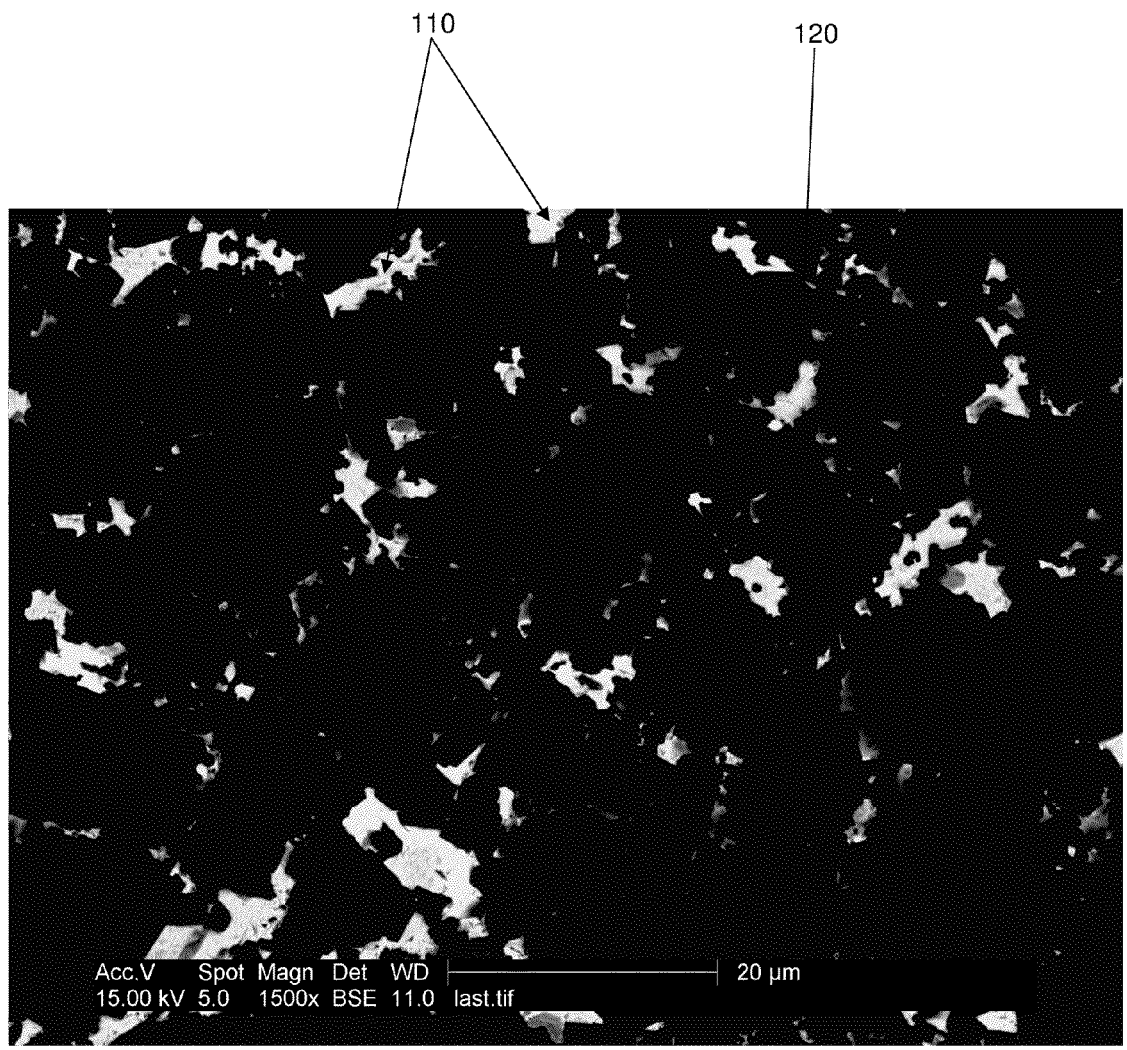
FIG. 8a shows a micrograph of a diamond layer of a PCD part.
Figure 8B:
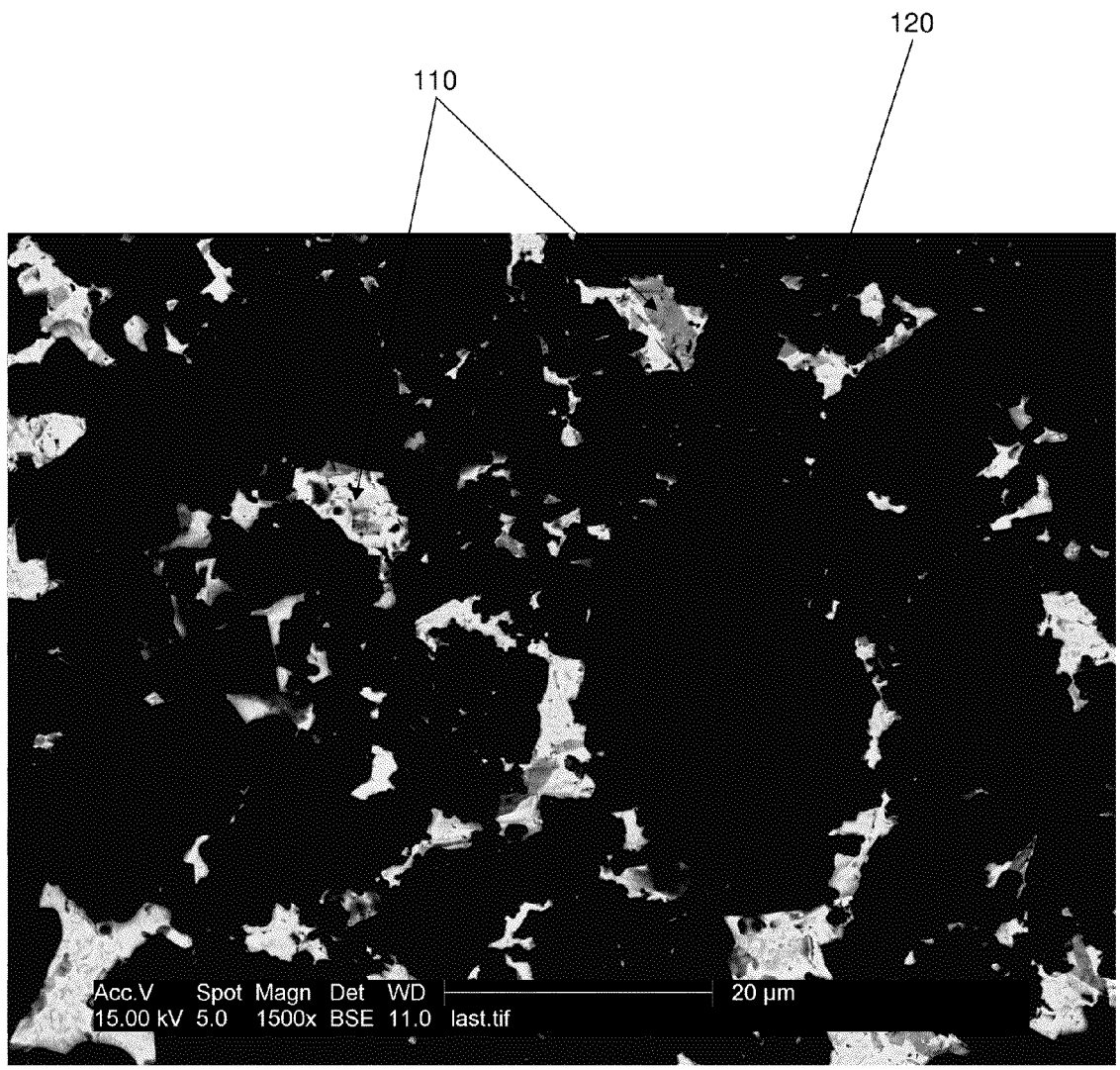
FIG. 8b shows a micrograph of a diamond layer of a PCD part.
Figure 8C:
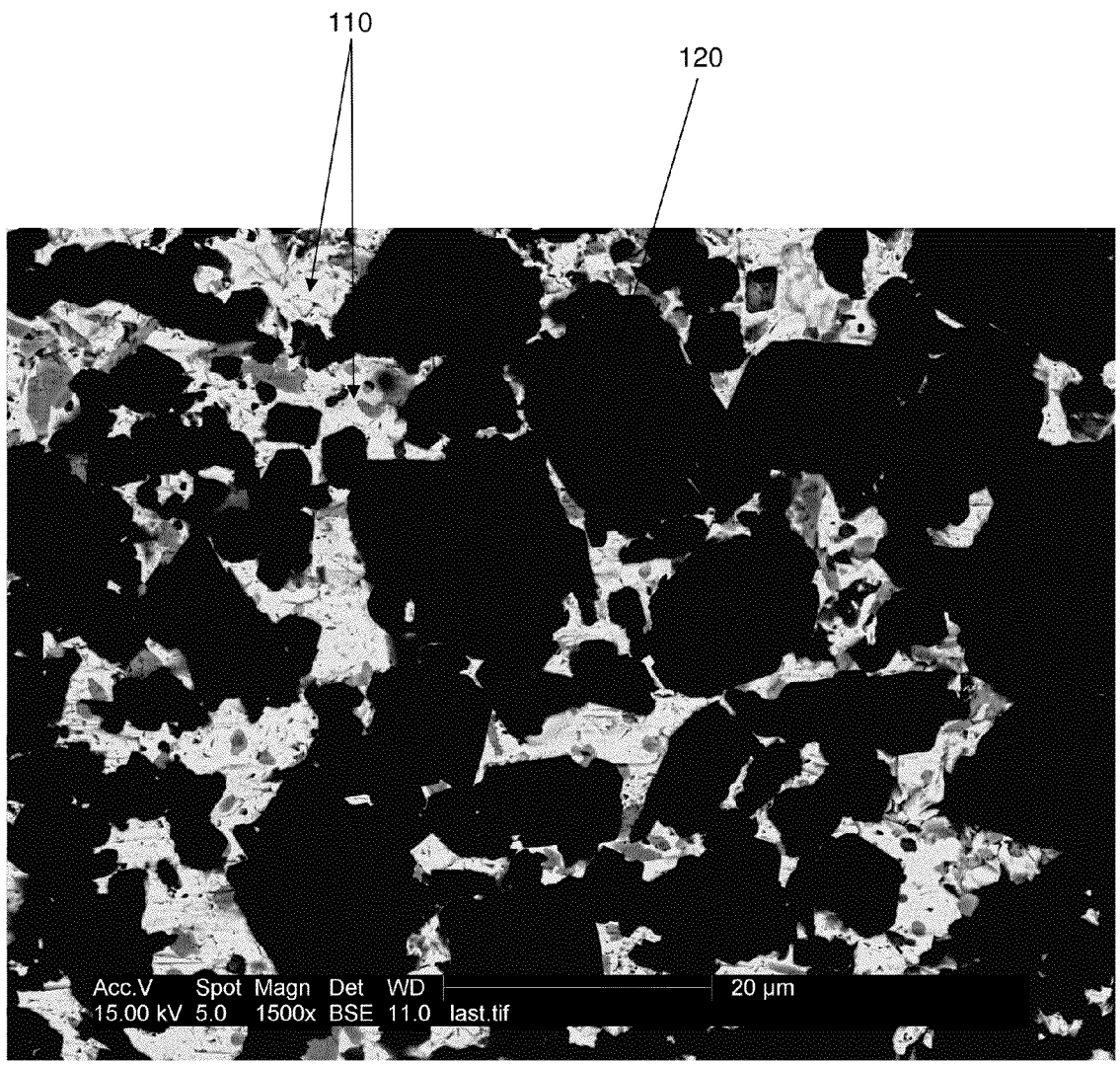
FIG. 8c shows a micrograph of a diamond layer of a PCD part.

Micrographs of the outer, middle, and inner diamond layers are shown in FIGS. 8a, 8b, and 8c respectively, illustrating the solvent metal pores 110 (in lighter grey) and the diamond crystals 120 (in black). Each of the diamond layers was analyzed as discussed above to determine the pore size. The outer diamond layer had a mean maximum pore length of 5.9 microns. The middle diamond layer had a mean maximum pore length of 8.53 microns. The inner diamond layer had a mean maximum pore length of 17.56 microns. One important observation is that no significant micro cracks can be observed in FIG. 8c (the inner diamond layer). The PCD parts were cut to expose all layers of the PCD and were elution tested in a Hanks solution with the pH buffered to 6.0. The average metal ion levels in the Hanks solution over five days of testing were 0.65 ppm, 0.54 ppm, 0.57 ppm, 0.38 ppm, and 0.45 ppm respectively. The elution data shows more than an eleven fold decrease in metal ions released from the PCD part achieved by limiting the pore size of the PCD material.

Figure 9:
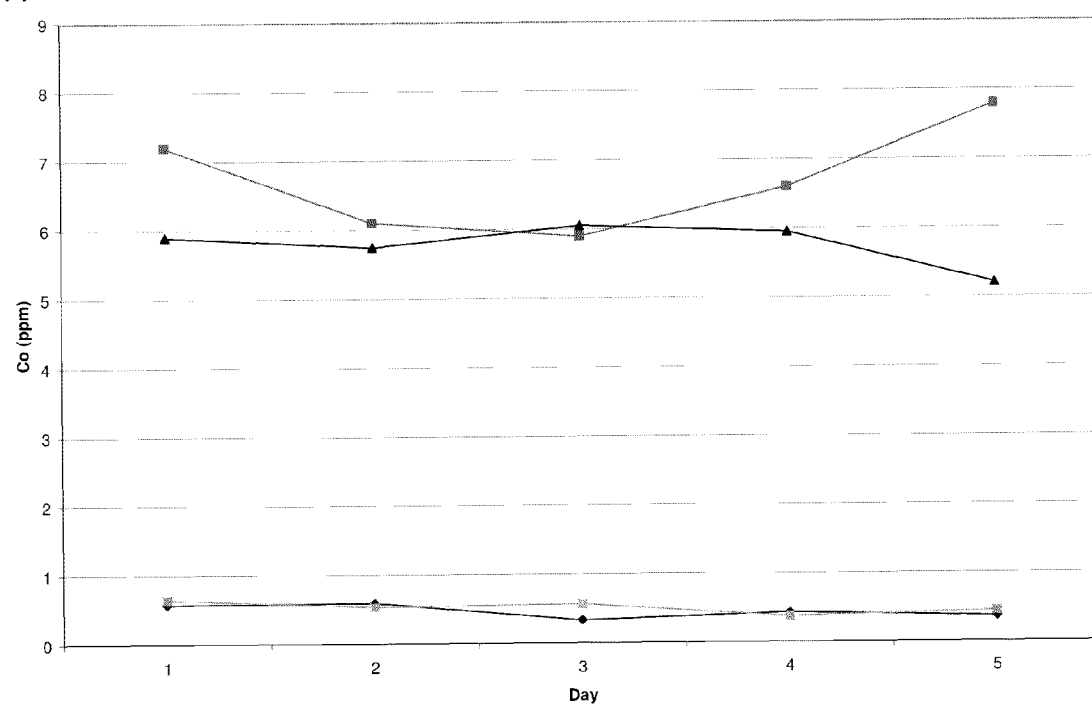
FIG. 9 shows a graph of daily Co elution for various PCD parts.
Figure 10:
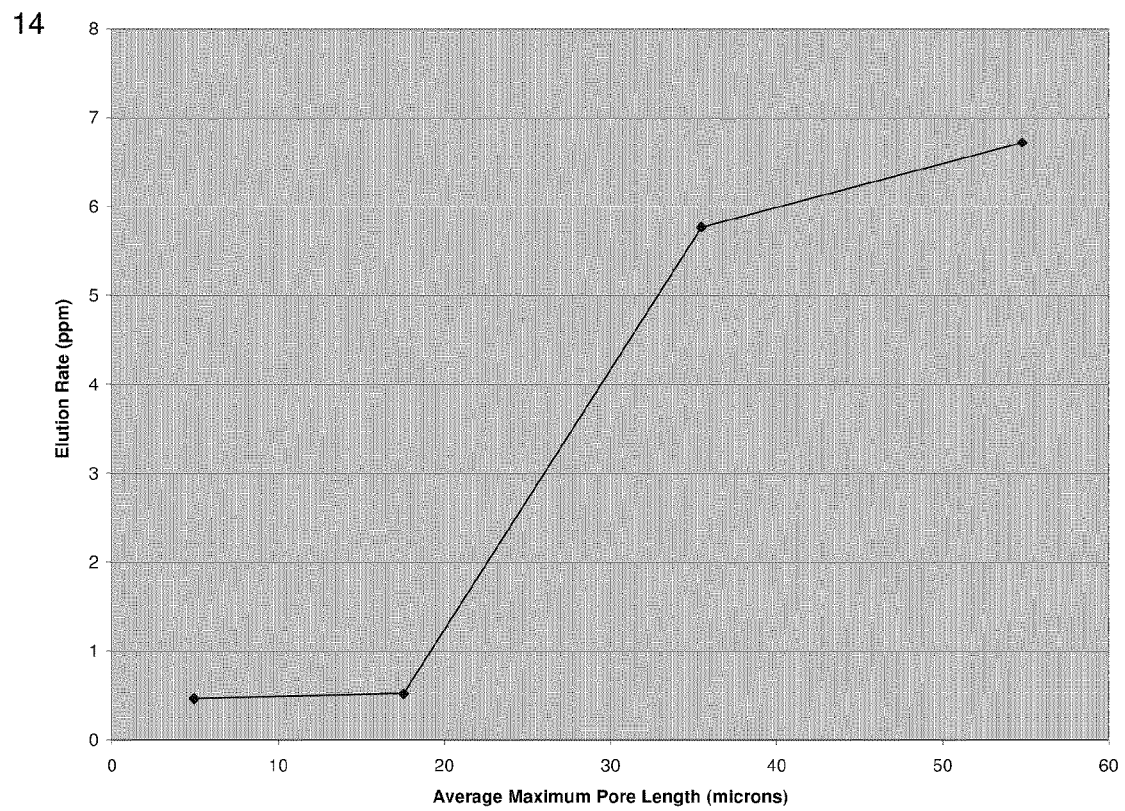
FIG. 10 shows a graph of daily metal ion elution for various solvent metal pore sizes.

FIGS. 9 and 10 graphically show the test data discussed above as regards the elution of metal ions for varying pore sizes. As is observed in FIG. 9, those PCD parts which included one or more diamond layers with larger solvent metal pore sizes resulted in concentrations of metal ions between about 6 and 7 ppm in the Hanks solution. In contrast, those PCD parts which had smaller pore sizes in all exposed diamond layers produced concentrations of metal ions of approximately 0.5 ppm in the Hanks solution. There is thus a significant reduction in ionic elution rate when the solvent metal pore size remains below a certain average maximum pore length. It is currently understood that the reason for this is the reduction in solidification cracking seen as micro cracks in the solvent metal in those PCD pores which are larger.

FIG. 10 shows a chart of the elution rate of metal ions into the Hanks solution versus the average maximum pore length. It can be seen how the elution rate for small pore sizes remains relatively constant at approximately 0.5 ppm and then sharply increases as the pore size increases past about 20 microns. Thus, corrosion can be virtually eliminated by producing PCD parts which do not have exposed diamond layers with average pore sizes greater than 20 microns.

As evidenced by the above examples, the pore size may be controlled by modifying the mixture of diamond crystal sizes that are used in the particular diamond layer so that the pore length is limited. Thus, rather than using only larger diamond crystals in the gradient transitional (inner) diamond layers, a mixture of larger and smaller diamond crystals are used. The use of a mixture of multiple diamond sizes in diamond layer results in the smaller diamond sizes breaking up the larger interstitial pores into multiple, smaller pores. In modifying the mixture of diamond crystal sizes, the overall percentages of diamond and metal in the diamond layer is not changed so that the coefficient of thermal expansion and the dilatation properties of the transitional diamond layer are also unchanged and are correct for proper stress and strength in the PCD construct.

As has been discussed, the substrate is typically formed of a metal or mixture of metal and metal carbides, and as such has a much higher coefficient of thermal expansion and dilation than diamond containing layers. As such, the inner diamond layer has a higher metal content so that the coefficient of thermal expansion and dilation are closer to that of the substrate. These inner gradient or transition diamond layer(s) thus provide a transition in physical properties between the substrate and the outer diamond layer, which has a higher diamond content. Such a transition between the substrate and the outer diamond layer avoids the high stress which would occur between an outer diamond layer bonded directly to the substrate. Such a high stress could weaken the PCD part or even cause the diamond layer to detach from the substrate.

It has thus been discovered that Sn may be used within a limited range as part of the sintering metal in the diamond layers in order to increase the biocompatibility of the resulting PCD part. Outside of the workable range, the Sn containing solvent metal did not sinter well and did not result in a PCD part with adequate strength or grind resistance. The Sn containing solvent metals achieved improved biocompatibility by addressing the carbide formation and phase separation problems that were discovered in PCD parts which used CoCrMo alloys as the solvent metal.

It has been further discovered that biocompatibility may be further improved by controlling the size of the solvent metal pores between the diamond crystals, particularly in the inner layers of the PCD part. While it was previously thought that the outer layer was primarily responsible for the biocompatibility of the PCD part, it has been discovered that the inner layers have a pronounced effect on the biocompatibility of the PCD part. The reduction in solvent metal pore sizes reduces and may substantially eliminate the occurrence of micro cracks as the temperature and pressure of the PCD part are reduced after sintering. These micro cracks produce areas of increased corrosion and the elimination of the cracks thus eliminates these points of increased corrosion.

The present invention provides a much greater reduction in corrosion and improvement in biocompatibility when the pore size control and improved Sn bearing solvent metal composition are used together. As discussed, Sn bearing solvent metals have increased coefficients of thermal expansion and dilation as compared to the CoCrMo alloys traditionally used for solvent metal. Thus, while the Sn containing solvent metal reduces corrosion, it typically increases the occurrence of micro cracks as compared to previous solvent metals and is thus hindered by the increased presence of micro cracks. When Sn based solvent metals are used with the traditionally large pore spaces, particularly in the exposed transitional layers of the PCD part, the Sn based solvent metal results in elevated release of metal ions during elution testing and does not improve the biocompatibility of the part. It is thus important to control the pore size in a PCD part which contains Sn in the solvent metal.

As is demonstrated by the examples above, a PCD part which includes the Sn containing solvent metal and which is constructed so as to have reduced pore sizes is significantly more corrosion resistant and biocompatible than previous PCD parts which used CoCrMo as the solvent metal even when the part is cut to expose the transitional layers of diamond. The transitional layers of diamond have much higher amounts of solvent metal, and it has been discovered that these layers, although exposed to a lesser degree than the outer layer, are more problematic in controlling the metal ions released therefrom. As demonstrated, limiting the pore size of the diamond layers, including the transitional diamond layers to less than about 25-30 microns is effective in significantly reducing the elution of metal ions from the part. Moreover, limiting the pore size of the exposed diamond layers to less than about 20 microns virtually eliminates the elution of metal ions from the part. The reduction of metal ion elution from the part is the largest component of improving the biocompatibility of the PCD part, as diamond wear is virtually nonexistent for a properly sintered part and the heavy metals released from the part may cause various bodily illnesses as well as rejection of the prosthetic part itself.

There is thus disclosed an improved sintered polycrystalline diamond compact. It will be appreciated that numerous changes may be made to the present invention without departing from the scope of the claims.

What is claimed is:

1. A sintered polycrystalline diamond compact for a prosthetic joint comprising:
   a sintered polycrystalline articulation diamond layer, the diamond layer forming an articulation surface for an artificial joint on a first side thereof, the diamond layer comprising a plurality of diamond crystals and a solvent metal disposed in interstitial pores between the diamond crystals; and wherein the solvent metal comprises about 33 to 50 percent Sn, about 38 to 45 percent Co, and about 10 to 19 percent Cr.

2. The compact of claim 1, wherein the interstitial pores of the diamond layer has a mean pore length defined as the average Feret's diameter of a group of the largest interstitial pores by pore area, the group being sufficiently large to include 80 percent of the surface area of the exposed interstitial pores; and wherein the mean pore length of the interstitial pores of the diamond layer is less than 30 microns.

3. The compact of claim 1, wherein the solvent metal comprises a mixture of Sn, Co, Cr, and Mo.

4. The compact of claim 3, wherein the solvent metal comprises about 33 to 50 percent Sn, about 38 to 45 percent Co, about 10 to 19 percent Cr, and up to about 4 percent Mo.

5. The compact of claim 3, wherein the solvent metal comprises about 44 to 48 percent Sn, about 38 to 42 percent Co, about 10 to 14 percent Cr, and up to about 4 percent Mo.

6. The compact of claim 3, wherein the solvent metal comprises about 46 percent Sn, about 40 percent Co, about 12 percent Cr, and about 2 percent Mo.

7. The compact of claim 1, wherein the compact comprises a transitional diamond layer attached to a second side of the articulation diamond layer, the transitional diamond layer having diamond crystals and solvent metal disposed in the interstitial pores between the diamond crystals;

wherein the interstitial pores of the diamond layers have a mean pore length defined as the average Feret's diameter of a group of the largest interstitial pores by pore area, the group being sufficiently large to include 80 percent of the surface area of the exposed interstitial pores; and wherein the mean pore length of the interstitial pores of both diamond layers is less than 30 microns.

8. The compact of claim 1, wherein the compact comprises a transitional diamond layer attached to a second side of the articulation diamond layer, the transitional diamond layer having diamond crystals and solvent metal disposed in interstitial pores between the diamond crystals; and wherein the transitional diamond layer comprises approximately 50 percent diamond by volume, and wherein said diamond comprises about 50 percent of 40 micron diamond crystals, about 38 percent of 20 micron diamond crystals, and about 12 percent of 4 to 8 micron diamond crystals.

9. The compact of claim 1, wherein the compact comprises a transitional diamond layer attached to a second side of the articulation diamond layer, the transitional diamond layer having diamond crystals and solvent metal disposed in interstitial pores between the diamond crystals; and wherein the transitional diamond layer comprises approximately 40 percent diamond by volume, and wherein said diamond comprises about 65 percent of 20 micron diamond crystals, about 15 percent of 10 micron diamond crystals, and about 20 percent of 4 to 8 micron diamond crystals.

10. The compact of claim 1, wherein the compact comprises a first transitional diamond layer attached to the articulation diamond layer and a second transitional diamond layer attached to the first transitional diamond layer, the first and second transitional diamond layers having diamond crystals and solvent metal disposed in the interstitial pores between the diamond crystals;

wherein the first transitional diamond layer comprises approximately 50 percent diamond by volume, and wherein said diamond comprises about 50 percent of 40 micron diamond crystals, about 38 percent of 20 micron diamond crystals, and about 12 percent of 4 to 8 micron diamond crystals; and wherein the second transitional diamond layer comprises approximately 40 percent diamond by volume, and wherein said diamond comprises about 65 percent of 20 micron diamond crystals, about 15 percent of 10 micron diamond crystals, and about 20 percent of 4 to 8 micron diamond crystals.

11. A sintered diamond polycrystalline compact comprising:

an outer articulation diamond layer, the articulation diamond layer forming an articulation surface thereon, the articulation diamond layer having a plurality of diamond crystals therein and solvent metal disposed in interstitial pores between the diamond crystals;

an inner first transitional diamond layer attached to the articulation diamond layer, the first transitional diamond layer having a plurality of diamond crystals therein and solvent metal disposed in interstitial pores between the diamond crystals; and wherein the interstitial pores of the diamond layers have a mean pore length defined as the average Feret's diameter of a group of the largest interstitial pores by pore area, the group being sufficiently large to include 80 percent of the surface area of the exposed interstitial pores; and wherein the mean pore length of the interstitial pores of both diamond layers is less than 30 microns; and wherein the solvent metal has a composition of about 33 to 50 percent Sn, about 38 to 45 percent Co, about 10 to 19 percent Cr, and about 0 to 4 percent Mo.

12. The compact of claim 11, wherein the mean pore length is less than 20 microns.

13. The compact of claim 11, wherein the transitional diamond layer comprises approximately 50 percent diamond by volume, and wherein said diamond comprises about 50 percent of 40 micron diamond crystals, about 38 percent of 20 micron diamond crystals, and about 12 percent of 4 to 8 micron diamond crystals.

14. The compact of claim 13, further comprising a second transitional diamond layer attached to the first transitional diamond layer, and wherein the second transitional diamond layer comprises approximately 40 percent diamond by volume, and wherein said diamond comprises about 65 percent of 20 micron diamond crystals, about 15 percent of 10 micron diamond crystals, and about 20 percent of 4 to 8 micron diamond crystals.

15. The compact of claim 11, wherein the first transitional diamond layer approximately 40 percent diamond by volume, and wherein said diamond comprises about 65 percent of 20 micron diamond crystals, about 15 percent of 10 micron diamond crystals, and about 20 percent of 4 to 8 micron diamond crystals.

16. The compact of claim 11, wherein the articulation diamond layer approximately 80 percent diamond by volume, and wherein said diamond comprises about 75 percent of 20 micron diamond crystals and about 25 percent of 4 to 8 micron diamond crystals.

17. A sintered polycrystalline diamond compact comprising:

an outer articulation diamond layer, the articulation diamond layer forming an articulation surface thereon, the articulation diamond layer having a plurality of diamond crystals therein and solvent metal disposed in interstitial pores between the diamond crystals; and wherein the solvent metal has a composition of about 33 to 50 percent Sn, about 38 to 45 percent Co, about 10 to 19 percent Cr, and about 0 to 4 percent Mo.

18. The compact of claim 17, wherein the solvent metal has a composition of about 44 to 48 percent Sn, about 38 to 42 percent Co, about 10 to 14 percent Cr, and about 0 to 4 percent Mo.

19. The compact of claim 17, wherein the solvent metal has a composition of about 46 percent Sn, about 40 percent Co, about 12 percent Cr, and about 2 percent Mo.

20. The compact of claim 17, further comprising:
an inner first transitional diamond layer attached to the articulation diamond layer, the first transitional diamond layer having a plurality of diamond crystals therein and solvent metal disposed in the interstitial pores between the diamond crystals; and
wherein the interstitial pores of the diamond layers have a mean pore length defined as the average Feret's diameter of a group of the largest interstitial pores by pore area, the group being sufficiently large to include 80 percent of the surface area of the exposed interstitial pores; and
wherein the mean pore length of the interstitial pores of both diamond layers is less than 30 microns.

21. The compact of claim 20, wherein the articulation diamond layer approximately 80 percent diamond by volume, and wherein said diamond comprises about 75 percent of 20 micron diamond crystals and about 25 percent of 4 to 8 micron diamond crystals; and
wherein the first transitional diamond layer comprises approximately 50 percent diamond by volume, and wherein said diamond comprises about 50 percent of 40 micron diamond crystals, about 38 percent of 20 micron diamond crystals, and about 12 percent of 4 to 8 micron diamond crystals.

22. The compact of claim 21, further comprising a second transitional diamond layer attached to the first transitional diamond layer, and wherein the second transitional diamond layer comprises approximately 40 percent diamond by volume, and wherein said diamond comprises about 65 percent of 20 micron diamond crystals, about 15 percent of 10 micron diamond crystals, and about 20 percent of 4 to 8 micron diamond crystals.

23. The compact of claim 20, wherein the articulation diamond layer approximately 80 percent diamond by volume, and wherein said diamond comprises about 75 percent of 20 micron diamond crystals and about 25 percent of 4 to 8 micron diamond crystals; and
wherein the first transitional diamond layer comprises approximately 40 percent diamond by volume, and wherein said diamond comprises about 65 percent of 20 micron diamond crystals, about 15 percent of 10 micron diamond crystals, and about 20 percent of 4 to 8 micron diamond crystals.

* * * * *